United States Patent
Hladio et al.

(10) Patent No.: US 11,612,443 B2
(45) Date of Patent: Mar. 28, 2023

(54) SYSTEMS, METHODS AND DEVICES TO SCAN 3D SURFACES FOR INTRA-OPERATIVE LOCALIZATION

(71) Applicant: INTELLIJOINT SURGICAL INC., Kitchener (CA)

(72) Inventors: Andre Novomir Hladio, Waterloo (CA); Richard Tyler Fanson, Stoney Creek (CA); Luke Becker, Kitchener (CA); Arash Abadpour, Toronto (CA); Joseph Arthur Schipper, Kitchener (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 0 days.

(21) Appl. No.: 17/849,017

(22) Filed: Jun. 24, 2022

(65) Prior Publication Data
US 2022/0331016 A1 Oct. 20, 2022

Related U.S. Application Data

(63) Continuation of application No. 16/097,410, filed as application No. PCT/CA2017/000104 on Apr. 28, 2017, now Pat. No. 11,432,878.

(Continued)

(51) Int. Cl.
*A61B 34/20* (2016.01)
*A61B 90/30* (2016.01)
(Continued)

(52) U.S. Cl.
CPC ............. *A61B 34/20* (2016.02); *A61B 90/14* (2016.02); *A61B 90/30* (2016.02); *A61B 90/361* (2016.02);
(Continued)

(58) Field of Classification Search
CPC ......... A61B 34/20; A61B 90/14; A61B 90/30; A61B 90/361; A61B 2034/107;
(Continued)

(56) References Cited

U.S. PATENT DOCUMENTS

2010/0069919 A1   3/2010   Carls et al.
2016/0191887 A1*  6/2016   Casas ............... A61B 34/10
                                                   348/47

(Continued)

FOREIGN PATENT DOCUMENTS

WO   2006075331 A2   7/2006
WO   2006128301 A1   12/2006
WO   2016065457 A1   5/2016

OTHER PUBLICATIONS

International Search Report dated Aug. 15, 2017 for Corresponding International PCT Patent Application No. PCT/CA2017/000104; 3 Pages.

(Continued)

*Primary Examiner* — Kevin T Truong
*Assistant Examiner* — Diana Jones

(57) ABSTRACT

Systems and methods are described herein to generate a 3D surface scan of a surface profile of a patient's anatomy. The 3D surface scan may be generated by reflections of structured light off the surface profile of the anatomy. The 3D surface scan may be used during intra-operative surgical navigation by a localization system. Optionally, a pre-operative medical image may also be registered to the localization system or used to enhance the 3D surface scan.

19 Claims, 24 Drawing Sheets

Related U.S. Application Data

(60) Provisional application No. 62/395,682, filed on Sep. 16, 2016, provisional application No. 62/328,978, filed on Apr. 28, 2016.

(51) Int. Cl.
*A61B 90/14* (2016.01)
*G06T 7/30* (2017.01)
*A61B 90/00* (2016.01)
*G06T 7/73* (2017.01)
*G06T 7/33* (2017.01)
*A61B 34/10* (2016.01)
*A61B 18/00* (2006.01)
*A61B 90/50* (2016.01)

(52) U.S. Cl.
CPC ............ *G06T 7/30* (2017.01); *G06T 7/337* (2017.01); *G06T 7/74* (2017.01); *A61B 2018/00577* (2013.01); *A61B 2034/107* (2016.02); *A61B 2034/2048* (2016.02); *A61B 2034/2057* (2016.02); *A61B 2034/2065* (2016.02); *A61B 2090/364* (2016.02); *A61B 2090/373* (2016.02); *A61B 2090/3937* (2016.02); *A61B 2090/3983* (2016.02); *A61B 2090/502* (2016.02); *G06T 2200/04* (2013.01); *G06T 2207/10028* (2013.01); *G06T 2207/10081* (2013.01); *G06T 2207/10088* (2013.01); *G06T 2207/30016* (2013.01); *G06T 2207/30204* (2013.01)

(58) Field of Classification Search
CPC .... A61B 2034/2057; A61B 2034/2065; A61B 2090/364; A61B 2090/373; A61B 2090/3937; A61B 2018/00577; G06T 7/74; G06T 7/30; G06T 7/337; G06T 2200/04; G06T 2207/10028; G06T 2207/10081; G06T 2207/10088; G06T 2207/30016; G06T 2207/30204
See application file for complete search history.

(56) References Cited

U.S. PATENT DOCUMENTS

2017/0296292 A1* 10/2017 Mahmood .............. A61B 34/20
2017/0348061 A1* 12/2017 Joshi .................. A61B 10/0275

OTHER PUBLICATIONS

Written Opinion dated Aug. 15, 2017 for Corresponding International PCT Patent Application No. PCT/CA2017/000104; 3 Pages.

* cited by examiner ns, METHODS AND DEVICES TO
SCAN 3D SURFACES FOR
INTRA-OPERATIVE LOCALIZATION

CROSS-REFERENCE TO RELATED APPLICATIONS

This application is a continuation of U.S. application Ser. No. 16/097,410 titled "Systems, Methods and Devices to Scan 3D Surfaces for Intra-Operative Localization" and filed Apr. 28, 2017. Application Ser. No. 16/097,410 is a 371 of PCT/CA2017/000104 filed Apr. 28, 2017. PCT/CA2017/000104 claims the benefit of U.S. provisional application No. 62/328,978 titled "Systems and methods to perform image registration and scan 3D surfaces for intra-operative localization" and filed on Apr. 28, 2016, and U.S. provisional application No. 62/395,682 titled "Systems and methods to perform image registration and scan 3D surfaces for intra-operative localization" and filed on Sep. 16, 2016. The entire contents of all applications listed above are incorporated herein by reference.

FIELD

The present specification relates to systems, methods and devices to generate a 3D surface scan of a patient's anatomy and use it for intra-operative localization during a surgical procedure.

BACKGROUND 3D scanning of a patient's anatomy to generate a 3D surface scan can be advantageous for use in surgical procedures. In particular, the 3D surface scan may then be provided to a localization system for use in computer navigated surgeries.

SUMMARY

Systems, devices and methods are described herein to generate a 3D surface scan of a surface profile of a patient's anatomy. The 3D surface scan may be generated by reflections of structured light off the surface profile of the anatomy. The 3D surface scan may be used during intra-operative surgical navigation by a localization system. Optionally, a pre-operative medical image may also be registered to the localization system or used to enhance the 3D surface scan.

There is described a computer implemented method to register a 3D surface scan of a surface profile of a patient's anatomy to a localization system comprising the steps of: receiving, by at least one processing unit, scanning extrinsic parameter data with respect to a scanning reference element in a fixed position relative to the anatomy, the scanning extrinsic parameter data being tracking data that can be used to calculate a scanning position and orientation; receiving, by the at least one processing unit, from a camera 3D scan data comprising images from a plurality of vantage points of structured light reflected off a surface of the patient's anatomy; generating, by the at least one processing unit, scanning extrinsic parameters representing the scanning position and orientation of the camera with respect to the scanning reference element using the scanning extrinsic parameter data; generating, by the at least one processing unit, a 3D surface scan of the surface profile of the anatomy with respect to the scanning reference element using the scanning extrinsic parameters and 3D scan data; receiving, by the at least one processing unit, registration extrinsic parameter data with respect to a localization reference element of a localization system, the registration extrinsic parameter data being tracking data that can be used to calculate a registration position and orientation; generating, by the at least one processing unit, registration extrinsic parameters representing the registration position and orientation of the localization reference element with respect to the scanning reference element from the registration extrinsic parameter data; registering, by the at least one processing unit, the 3D surface scan using the registration extrinsic parameters to the localization system to allow intra-operative navigation with respect to the 3D surface scan of the anatomy.

The method may further comprising, following registering, providing intra-operative navigation of a surgical instrument with respect to the 3D surface scan of the anatomy wherein a navigation tracker is attached to the surgical instrument. The method may comprise tracking a location of the surgical instrument using images of the navigation tracker and presenting, relative to the 3D surface scan, the location, location information derived therefrom or both the location and the location information.

The structured light may be projected by a structured light projector. The method may further comprise determining a positional relationship between the camera and the structured light projector to co-register the camera to the structured light projector. Determining the positional relationship between the camera and the structured light projector may comprise determining a position and orientation of calibration features using the camera, the features having a known positional relationship to the structured light projector.

The scanning reference element and the localization reference element may be a single reference element.

The method may further comprise receiving a medical image of the anatomy and using the medical image to compute and remove outliers in the 3D surface scan/3D point cloud.

The method may further comprising receiving a medical image of the anatomy and registering the medical image of the anatomy to the 3D surface scan to determine an optimal mapping between the medical image and the 3D surface scan. The step of registering the medical image of the anatomy to the 3D surface scan may comprise: receiving input to identify anatomical landmarks on the anatomy in a localization system coordinate frame of the localization system; receiving input to identify locations on the medical image corresponding to the anatomical landmarks in an image coordinate frame of the medical image; and determining a transformation to map the anatomical landmarks to the identified locations in the respective coordinate frames.

The method may further comprise the step of generating real time visual feedback to display on a display unit, the visual feedback comprising at least one of: a camera feed comprising a field of view of the camera while the anatomy is being scanned; graphics to visually emphasize at least one of the detected structured light, the localization reference element and the scanning reference element; a graphical representation of the 3D surface scan comprising a partially complete real time 3D surface scan; and a visual representation of metrics representing registration data criteria for the anatomy. The registration data criteria may be at least one of a correlation of aggregate 3D scan data with an expected surface profile of the anatomy, spatial and/or angular coverage of 3D scan data with respect to the anatomy, and density of 3D scan data with respect to anatomy.

Receiving scanning extrinsic parameter data may comprise receiving tracker data of a tracker and the step of generating scanning extrinsic parameters comprises generating a position and orientation of the camera with respect to the scanning reference element using the tracker data.

There is described a computer implemented method to provide position and orientation measurements of a surgical instrument with respect to a 3D surface scan of an anatomy comprising the steps of: receiving, by at least one processing unit, a 3D surface scan of the anatomy with respect to a scanning reference element; receiving, by the at least one processing unit, registration extrinsic parameter data with respect to a localization reference element, the registration extrinsic parameter data being tracking data that can be used to calculate a registration position and orientation; generating, by the at least one processing unit, registration extrinsic parameters representing the registration position and orientation of the localization reference element with respect to the scanning reference element from the registration extrinsic parameter data; registering, by the at least one processing unit, the 3D surface scan to the localization reference element using the registration extrinsic parameters; and providing, by the at least one processing unit, position and orientation measurements of the surgical instrument with respect the 3D surface scan of the anatomy.

Generating registration extrinsic parameters from the registration extrinsic parameter data may comprise generating a position and orientation measurement between the scanning reference element and the localization reference element.

The localization reference element and the scanning reference element may be a single reference element.

The localization reference element may be a tracker comprising optically detectable features and the localization system comprises at least one optical camera.

There is described a computer storage device storing instructions in a non-transient manner which instructions when executed configure one or more processing units to perform the computer implemented methods described herein.

There is described a computer system comprising one or more processing units coupled to at least one computer storage device storing instructions in a non-transient manner which instructions when executed configure the one or more processing units to perform the computer implemented methods described herein.

The computer system may comprising a 3D scanning system and a localization system wherein the 3D scanning system is configured to generate the 3D scan data and the scanning extrinsic parameters and the 3D surface scan, the 3D scan system configured to provide the 3D surface scan and to the localization system; wherein the localization system receives the 3D surface scan, generates the registration extrinsic parameters and registers the 3D surface scan; and wherein the computer system is configured according to one of: i) the 3D scanning system and localization system comprising separate systems which do not share components, each system comprising a respective one or more processing units coupled to a respective camera; and ii) the 3D scanning system and localization system comprising separate systems which do share components, each system comprising a respective one or more processing units and a single shared camera, the camera coupled to one of the separate systems at any one time; iii) the 3D scanning system and localization system provided by a single system of one or more processing units coupled to a camera.

The computer system may comprise a structured light projector and/or a camera.

BRIEF DESCRIPTION OF DRAWINGS

Embodiments disclosed herein will be more fully understood from the detailed description and the corresponding drawings, which form a part of this specification, and in which:

FIG. 2B, depicts a block diagram of components of a computer system showing additional components in accordance with an embodiment of the general framework of FIG. 2A while

Figure 1:
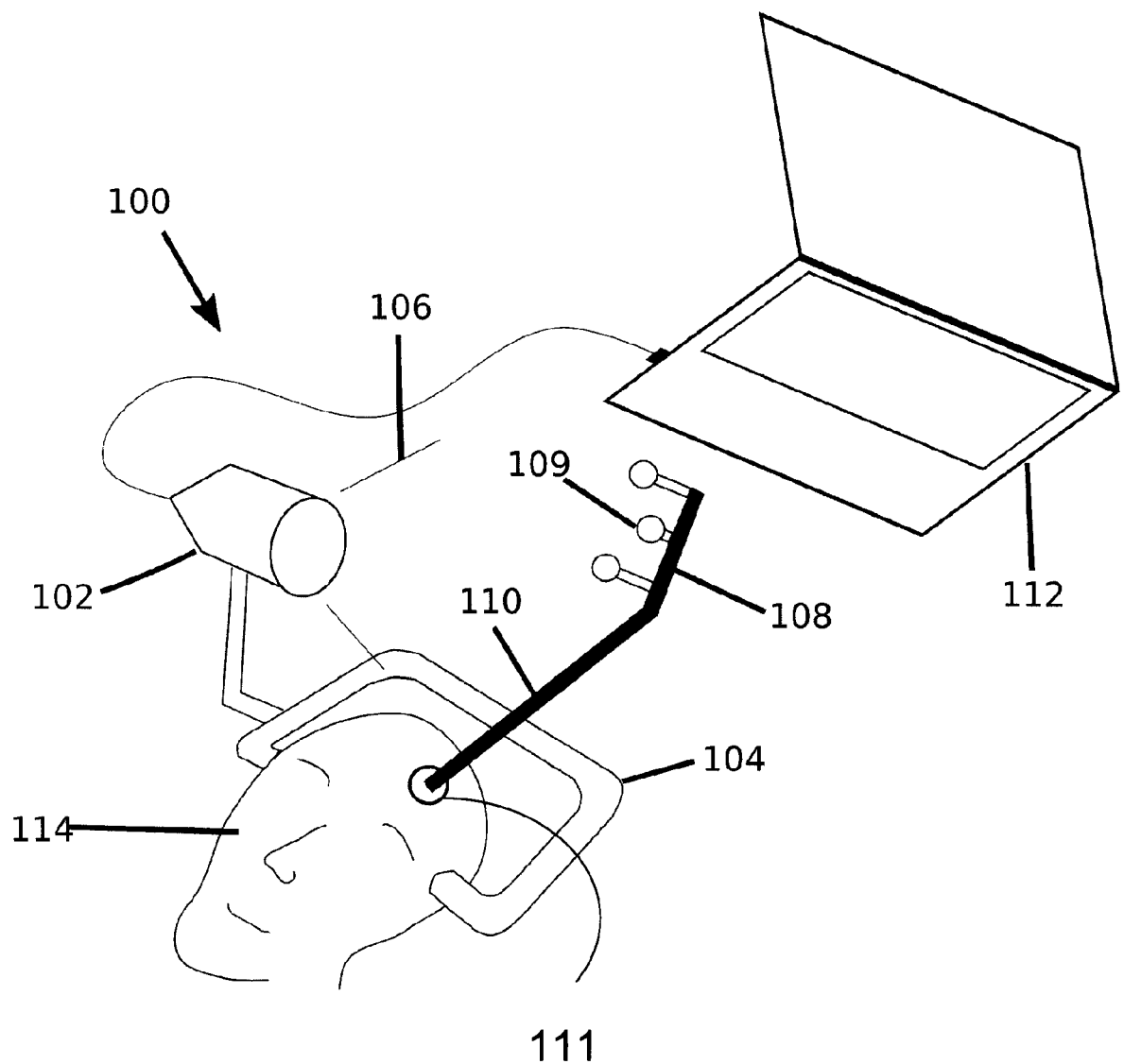
FIG. 1 illustrates, as an example for clarity, an intra-operative localization system in use on a patient's head.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

Several systems, methods and devices will be described below as embodiments. The scope of the claims should not be limited by the embodiments set forth in the examples, but should be given the broadest interpretation consistent with the description as a whole.

Accordingly, it is to be understood that this subject matter is not limited to particular embodiments described, and as such may vary. It is also to be understood that the terminology used herein is for the purpose of describing particular embodiments only, and is not intended to be limiting.

The following terms are used herein:

Extrinsic Parameters: generally refer to a pose (position and orientation) between two objects, when the pose is being used to calculate another measurement.

Extrinsic Parameter Data: refers to camera images that are used as the basis for extrinsic parameter calculation between the camera and the object it is tracking. The extrinsic parameters are computed from the extrinsic parameter data by a computing unit.

Tracker (aka Target): object that provides optically detectable features (by the camera) for pose calculation.

Intra-operative localization (aka navigation): tracking the position and orientation of objects (e.g. surgical tools) relative to a patient's anatomy in real time during surgery, for some therapeutic purpose.

Surface Profile: the shape and/or contour of a surface of an object, such as a patient's anatomy, in 3D space. The surface profile may be of a partial surface or surface of interest.

Registration: refers to the spatial transformation (sometimes referred to as spatial mapping) relating two or more coordinate systems (e.g. anatomical coordinate system, localization system coordinate system, image coordinate system). The registration may be a pose between two coordinate systems, and may be expressed, and represented in computer memory, according to any convenient convention (e.g. vectors, rotation matrices, homogeneous transformation matrix, Euler angles, quaternions, etc.).

Note: coordinate system and coordinate frame are synonyms in this document.

As will be apparent to those of skill in the art upon reading this disclosure, each of the individual embodiments described and illustrated herein has discrete components and features which may be readily separated from or combined with the features of any of the other several embodiments without departing from the teachings herein. Any recited method can be carried out in the order of events recited or in any other order which is logically possible. It is further understood that various methods described for performance by a computer system such as navigational surgery may be implemented in software such as instructions and data to configure at least one processing unit of a computer system to perform the method. The instructions and data may be stored in a device such as a memory (RAM, ROM, flash drive, etc.) or other non-transitory storage device (e.g.: magnetic, optical, or other disk or storage medium). A computing unit may comprise a laptop, workstation, or other computing device having at least one processing unit and at least one storage device such as memory storing software (instructions and/or data) as further described herein to configure the execution of the computing unit.

An exemplary intra-operative localization system 100 is shown in FIG. 1, in the context of a navigated cranial (brain) procedure. In this figure, a camera 102 is shown to be rigidly mounted to a head clamp 104, the camera oriented towards a surgical site such that its field of view 106 encompasses the surgical site. A tracker 108 is coupled to a probe 110, the tracker 108 providing optically detectable features 109 for tracking. The camera 102 transmits camera data including images of the tracker and the tracker's optically detectable features to a computing unit 112. The computing unit 112 performs steps to calculate a pose (position and orientation) of the probe 110 with respect to the patient's anatomy, in this case, the head 114. The computing unit 112 further displays, on a GUI, clinically relevant information to a surgeon. The computing unit 112 may also have access to medical image data from a medical image such as, an MRI of the head/brain, and may further register the image to the localization system in order to display navigational information relative to said medical image. Probe 110 may extend in head 114 via a craniotomy 111.

In this intra-operative localization system, the patient's anatomy is registered to a localization system coordinate frame. This means that the patient's anatomical planes, axes and/or features have a known positional relationship to the computing unit of the localization system. The localization system maintains the localization system coordinate frame for computations and displays relevant measurements in this computational space. The term registration, in the context of this specification, refers to a spatial transformation or a spatial mapping between two or more coordinate frames (e.g. anatomical coordinate frame, localization system coordinate frame, image coordinate frame, etc.). The registration may be in the form of a pose (position and orientation) between two coordinate frames. This pose may be expressed and represented in computer memory, according to any convenient convention (e.g. vectors, rotation matrices, homogeneous transformation matrix, euler angles, quaternions, etc.). The terms coordinate system and coordinate frame are synonymous in this specification.

A method to describe a workflow of a cranial procedure (including pre-operative setup steps) that uses the localization system is described herein. During pre-operative set-up of an intra-operative localization system, non-sterile instruments for registration and planning are calibrated (if necessary); medical images (e.g. from a MRI scan) of the patient's head may be loaded in to the computing unit of the localization system; and registration landmarks may be selected (optionally, depending on method of registration) on the patient's anatomy. This pre-operative set-up may be performed in advance of entering the operating room for the surgical procedure. Given the small, portable nature of the localization system described in FIG. 1, the pre-operative steps may be performed by a trained user off-site, at any convenient time or location.

Prior to the start of the cranial procedure, the patient and the intra-operative localization system are brought into the operating room. The patient's head may be immobilized via a head clamp or any other suitable means. A camera of the localization system may be mounted as shown in FIG. 1. In order to register the patient's head to the localization system coordinate frame, landmarks and/or features on the patient's head are localized to generate a registration between the camera and the patient's head. Optionally, a user may also register a medical image of the patient's head to the localization system coordinate frame. The process of identifying and localizing landmarks for registration may be conducted in two steps: (i) an initial set of landmarks on the anatomy may be selected to perform a coarse registration. A relatively small number of landmarks (at least 3 points, or two axes) are required to perform the coarse registration. (ii) a larger number of landmarks may be selected to perform a fine registration. This larger set of landmarks may be spread across the patient's head. The result is an accurate registration between the patient's anatomy, the localization system, and optionally the medical image. Where the patient has a particular alignment with respect to the direction of gravity (e.g. if patient is lying supine), and where the localization system provides inclination measurements (e.g. relative to a localization reference element) (as described in PCT/CA2015/000558 filed Oct. 29, 2015 by Hladio et al and titled "Systems, methods and devices for anatomical registration and surgical localization", the entire contents of which are incorporated herein by reference), the inclination measurements may be used for coarse registration.

Additionally, the registration between the anatomy and the localization system may be verified prior to performing the surgical procedure. For example, a check may be available in the computing unit to ensure that a virtual spatial representation (e.g. on a display unit) of a position and orientation of a tracked instrument relative to the patient's head matches a physical spatial position and orientation between the instrument and the patient's head as seen by a user. Next, details of the surgical intervention may be planned. For example, this step may include identifying a location of a craniotomy that would provide an optimal path towards a lesion to be resected and/or biopsied. Further, the patient may be prepared and draped in a sterile barrier. The camera of the localization system may be similarly draped without moving its position relative to the patient's head and sterile instruments for use during the surgery may be calibrated.

During the surgical procedure, a pose of at least one surgical instrument may be calculated and displayed in real-time in relation to a medical image (e.g. from the medical image data) to provide localization and navigational guidance to the user.

Further, an instrument may be calibrated during the surgical procedure. Calibrating an instrument generally refers to determining or confirming the spatial relationship between an effector of the instrument and a tracker associated with that instrument, the tracker being used by or a part of the localization system. Various tools/jigs/software routines may be used for instrument calibration. The effector of an instrument refers to a part of the instrument for which navigational information is useful. For example: the tip of a biopsy needle; the shaft axis of a probe; the axis, plane, pattern, etc. of a laser; the position and/or orientation of an implantable device.

A system to generate a 3D surface scan of an anatomy of a patient is described herein. The anatomy of the patient may comprise a surface profile, the profile having geometrical and positional attributes e.g. a certain shape with contours representing various features of the anatomy. The 3D surface scan represents the surface profile in digital format e.g. in the form of a 3D point cloud.

Figure 2A:
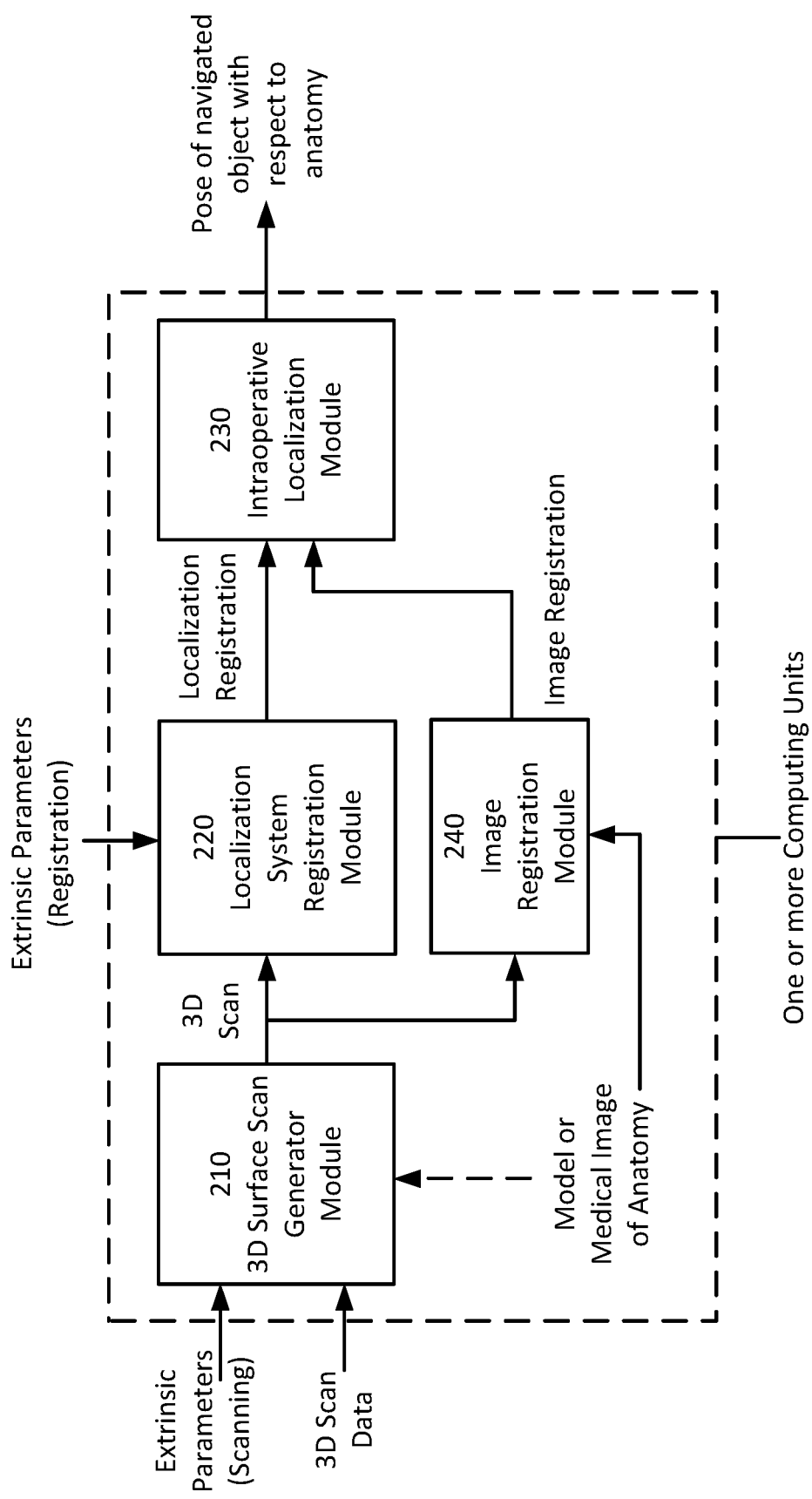
FIG. 2A depicts a block diagram of components of a computer system showing one or more modules of a general framework to provide intra-operative navigation with respect to a 3D surface scan.
Figure 2B:
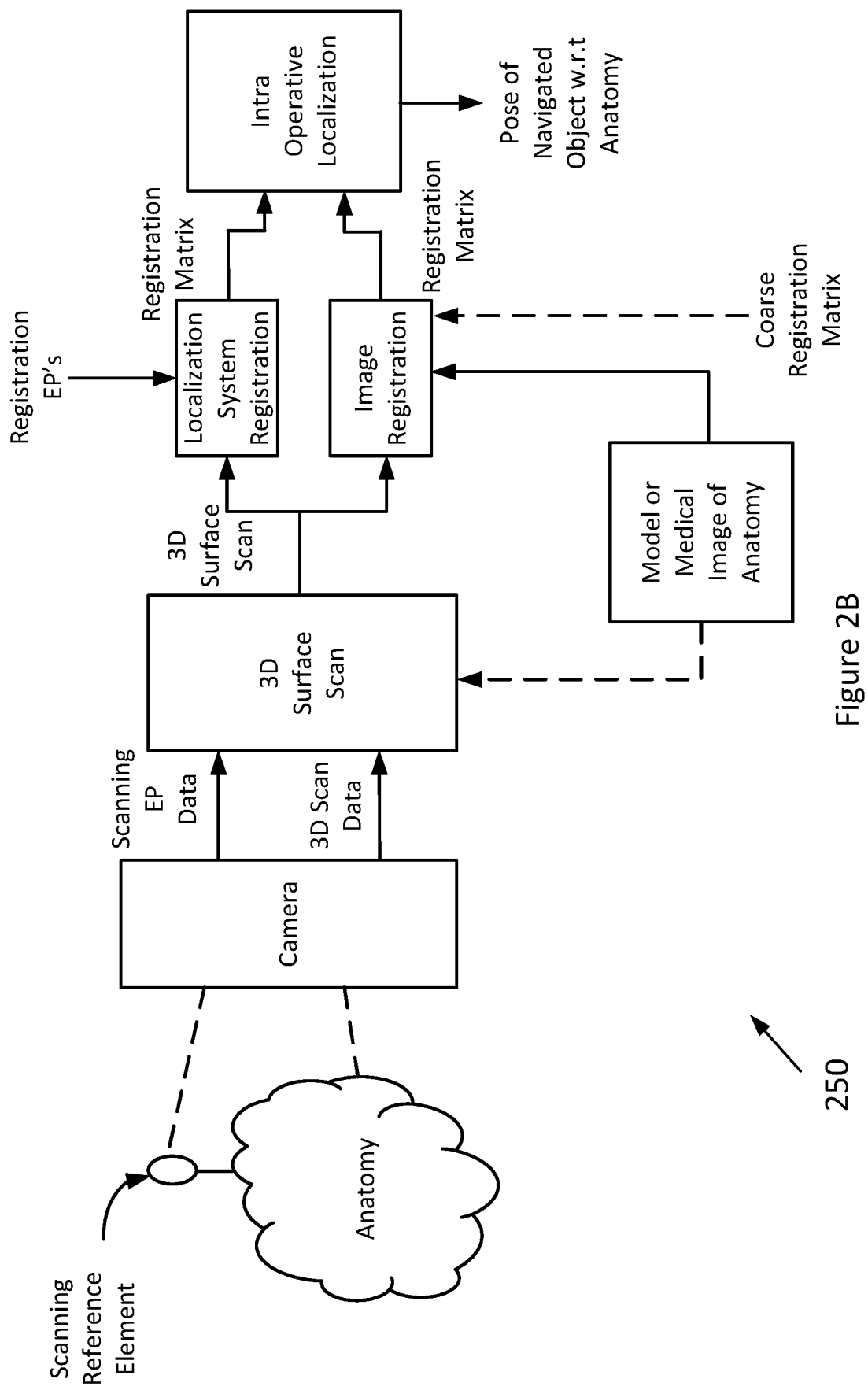
Figure 2C:
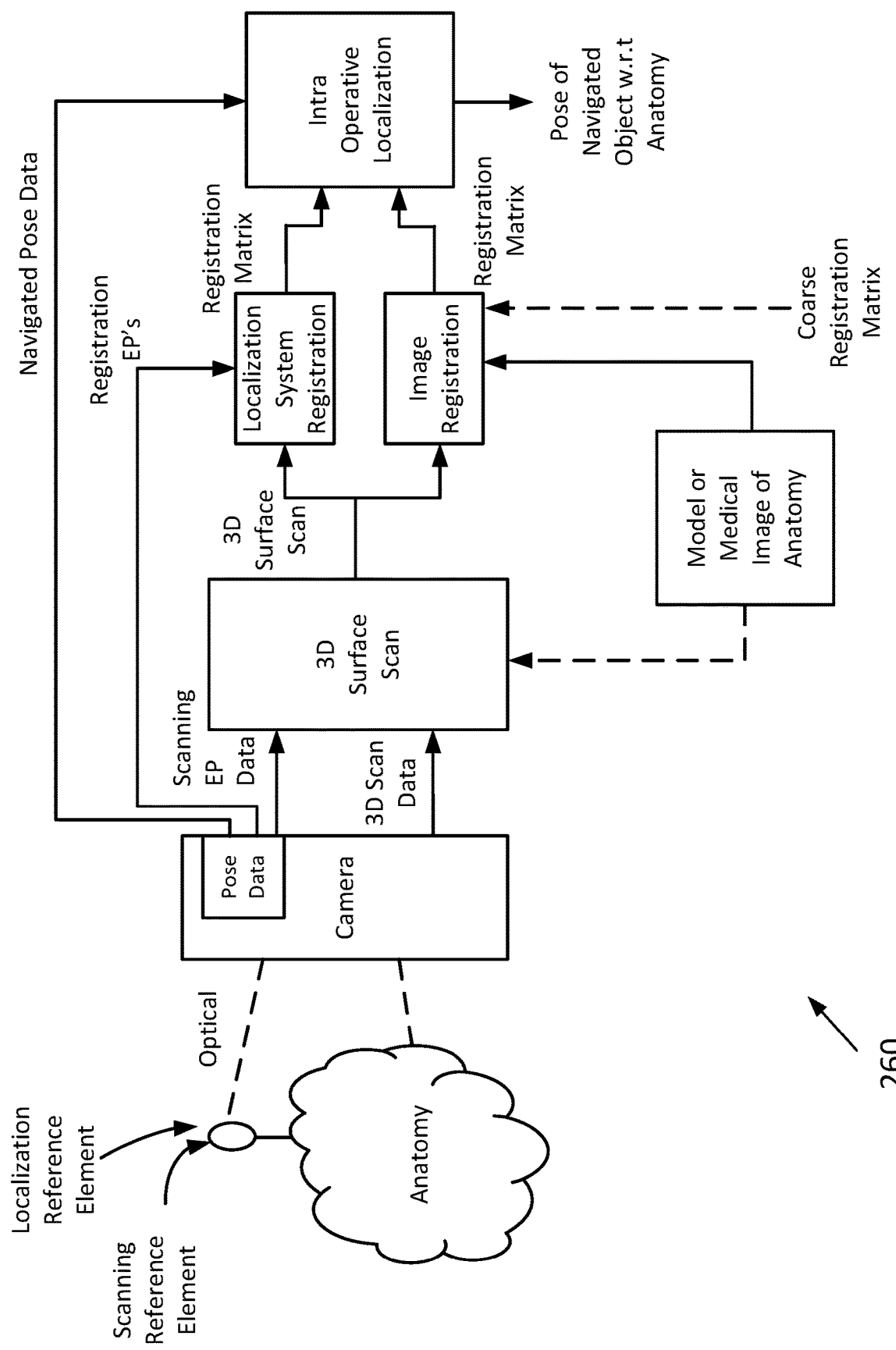
FIGS. 2C and 2D depict components of similar computer systems in accordance with embodiments configured for knee and cranial surgery, respectively.
Figure 2D:
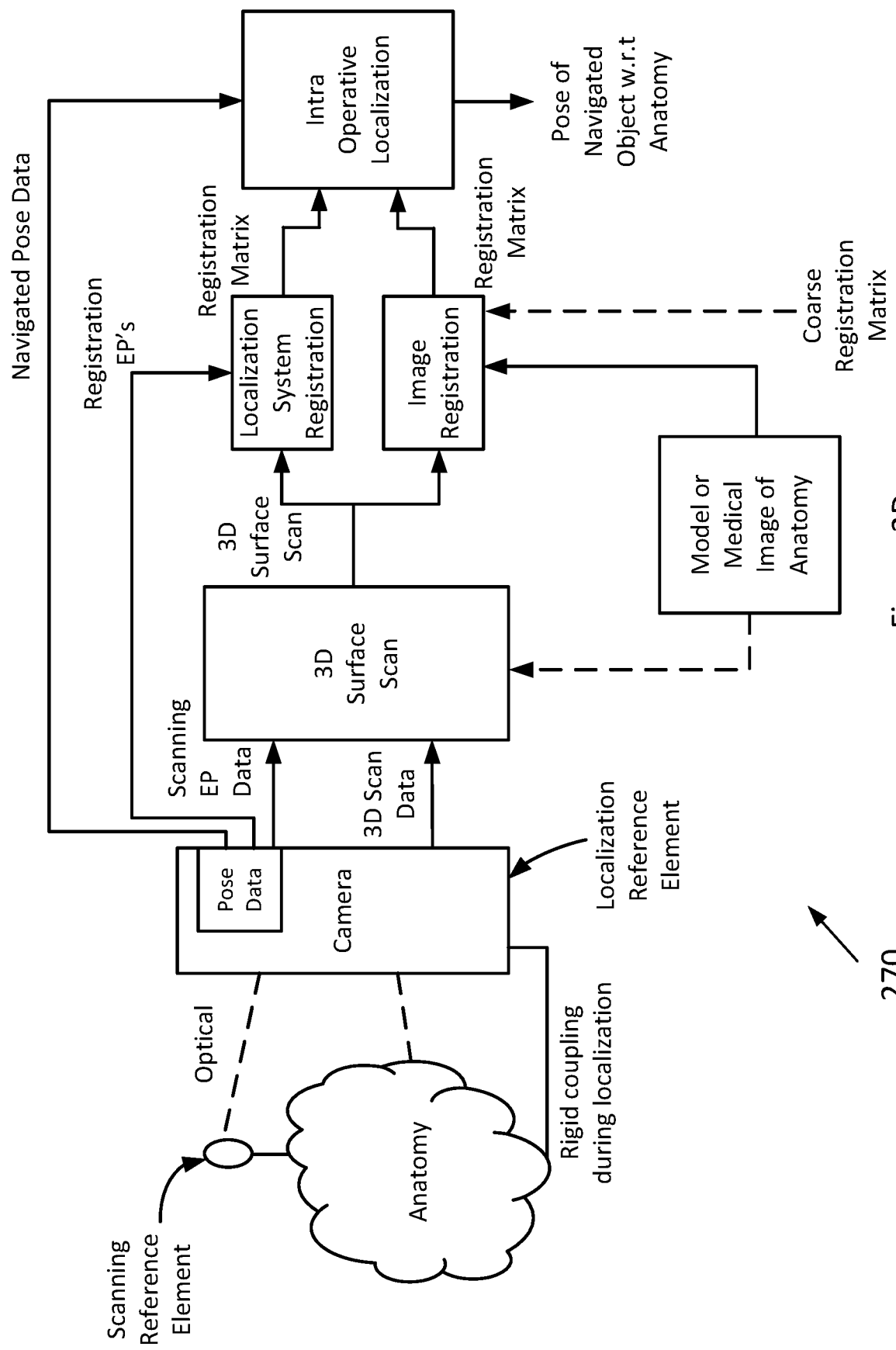

Referring now to FIG. 2A illustrating a block diagram of components of a computing system 200 showing computing modules 210, 220, 230 and 240 with inputs and outputs for performing a navigated surgery with respect to a 3D surface scan. The modules execute instructions to generate a 3D surface scan, register an image (optional), register the 3D surface scan to a localization system coordinate frame and calculate pose of an object by the localization system with respect to the 3D surface scan to provide navigation of the object. The modules may be software in storage devices such as a memory storing instructions coupled to one or more processing units. Additional components (e.g. peripheral components) of an example computing system 250 similar to system 200 are shown in FIG. 2B. FIG. 2B depicts a block diagram showing additional components in accordance with an embodiment of the general framework of FIG. 2A while FIGS. 2C and 2D depict additional components and modules of computer systems 260 and 270 similar to system 250 but configured for a use in accordance with a knee surgery embodiment and a cranial surgery embodiment, respectively. Additional components may be a camera, a scanning reference element for anatomy of a patient, and a localization reference element for anatomy of a patient as further described.

In 3D surface scan generator module 210, a 3D surface scan (typically in digital format) of a surface profile of a patient's anatomy is generated using 3D scan data of the anatomy and scanning extrinsic parameters with respect to a fixed reference on the anatomy (i.e. a scanning reference element). The scanning extrinsic parameters may be generated from scanning extrinsic parameter data received from a camera for example. When a tracker is used as a scanning reference element, a pose of the tracker may provide the scanning extrinsic parameters that represent a spatial relationship between the 3D surface scan and the scanning reference element.

3D scan data may be generated from images (e.g. provided by a camera), for example, a depth image at time t may produce a set of points $[P^S]_t$ with respect to the 3D scanning system. If the scanning extrinsic parameters $[T_E^S]_t$ are known, the points can be represented with respect to the scanning reference element according to $[P^E]_t = [T_E^S]_t^{-1} [P^S]_t$. If multiple depth images are captured, then a 3D surface scan $S^E$ with respect to the scanning reference element may be generated as the set of $[P^E]_t$ for all t i.e. at different instances in time. An exemplary depth image sensor such as, a camera may provide optical measurements or be sampled at regular intervals. Modern cameras can generate sequential measurements at a rate of 30 Hz, and faster.

In one implementation of the example above, the points $[P^S]_t$ can be generated by a laser of known geometry, properties and/or characteristics as described herein. The laser may project a plane such that a line is detected when pointed at a flat surface. An optical sensor with known characteristics can detect the laser reflected off the surface profile. While a position and orientation of the laser may be known with respect to the camera, an image comprising optical data may be captured with the camera. Computations are performed on the optical data to identify a subset of data that represents the laser to obtain an actual locus of 3D points generated by the laser (such as a plane). Additional computations generate an expected locus of 3D points which could produce the same optical data. The actual set of points and expected set of points are intersected and this intersection represents a set of 3D points $[P^S]_t$ on the object being scanned at time t.

The 3D surface scan $S^E$ generated by a computing unit of the scanning system may be in any digital form such as, a 3D point cloud. Optionally, a priori digital information generated through other means (e.g. in the form of a digital medical image and/or anatomical model, accessible in memory) representing an expected surface profile of the anatomy may be used to computationally enhance the 3D surface scan obtained in the step described above. The a priori information may also be used to filter out disturbances or measurement noise (such as background and/or unwanted digital data representing items other than anatomy) by comparing the expected surface profile with the 3D surface scan.

When scanning a patient's anatomy, 3D scan data not associated with the anatomy may be generated, such as measurement noise or scanning artifacts of objects in close proximity to the patient's anatomy (this data being referred to as disturbance data). The system may automatically detect disturbance data, and exclude it when computing the 3D surface scan. The system may use a priori knowledge of an expected surface profile to aid in filtering out the disturbance data. The system may provide a user with a view of the 3D scan data via a display, and the user may be able to manually filter out disturbances (e.g. using an input mechanism such as, a keyboard or mouse, and selecting the disturbance data to remove it from a representation of the 3D scan data).

A 3D surface scan and a corresponding model of the scanned surface may be provided as inputs to an outlier rejection module implemented in software. The outlier rejection module may employ computations to identify outliers (i.e. portions of the scanned surface that do not align with corresponding portions of the model) such as RANSAC, computations relating to image registration (described below), or other similar computations. The outlier rejection module may output a 3D surface scan where outliers are annotated to allow identification by a user (e.g. displaying in different colours). The outlier rejection module may output a 3D surface scan without including the outlier portions. The outlier rejection module may modify a 3D surface scan by predicting how the outlier portions would appear in the absence of a disturbance (e.g. by interpolating and/or extrapolating positional information based on the gradient of the regions surrounding the outlier portion).

In localization system registration module 220, the digital 3D surface scan of the surface profile of the anatomy is mapped to the localization system coordinate frame in a process called registration. The coordinate frame of the 3D surface scan is registered to the coordinate frame of the localization system using additional registration extrinsic parameters. These parameters can be generated by a computing unit of a localization system and are calculated with respect to the scanning extrinsic parameters that were used to generate the 3D surface scan.

Registration extrinsic parameters may be in the form of a pose measured by the localization system that has a known positional relationship with the 3D surface scan. For example, the registration extrinsic parameters may be the pose of the scanning reference element with respect to a localization reference element, where the fixed position of the scanning reference element is maintained during scanning and during registration. The scanning reference element has a known relationship with the 3D surface scan. The localization system may comprise a computing unit that receives registration extrinsic parameter data and generates registration extrinsic parameters or directly receives extrinsic parameters.

For an optical localization system, registration extrinsic parameter data may be in the form of an image from a camera, the camera also serving as a localization reference element, of a single tracker serving as a scanning reference element. The corresponding registration extrinsic parameters may be a positon and orientation of the tracker with respect to the camera. In another example, the scanning extrinsic parameters may be the pose of a scanning reference element that is fixed with respect to a patient's anatomy. The localization system may provide a localization reference element in the form of a second tracker that is fixed with respect to the patient's anatomy. A relative pose between the localization reference element and the scanning reference element may then be the registration extrinsic parameters. The computations performed by the computing unit are described herein. Where T is a matrix representing a spatial transformation or pose, $T_S^E$ is a pose of the 3D surface scan with respect to the scanning reference element, and $T_E^L$ is a pose of the scanning reference element with respect to the localization system coordinate frame, then the registration of the 3D surface scan to the localization system is $T_S^L = T_E^L T_S^E$. Alternatively, the pose of the localization system with respect to the 3D surface scan can be represented as $T_L^S = [T_S^L]^{-1}$. This illustrates a basic operation to register the 3D surface scan to the localization system. Intermediate or alternative transformations are also contemplated.

The pose of the 3D surface scan with respect to the scanning reference element may be known and stored in memory as data. Alternatively, the scanning reference element may define the 3D scanning coordinate system (i.e. $T_S^E$ is an identity matrix). In this case, the registration of the 3D surface scan to the localization system is equivalent to the registration extrinsic parameters.

In intraoperative localization module 230, registration of the 3D surface scan to the localization system enables the localization system to provide intra-operative localization or navigation of an object (e.g. a surgical tool) with respect to the 3D surface scan.

To further illustrate this example, where the localization system is an optical localization system, the scanning reference element and the localization reference element may be trackers comprising optically detectable markers. The computing unit of the localization system may receive image data of both reference elements, and use the data to generate respective poses of the scanning reference element and the localization reference element. The relative pose between the scanning reference element and the localization reference element may be the registration extrinsic parameters.

It is contemplated that the localization system and the scanning system may share the same hardware e.g. a single tracker may be used as the scanning reference element and the localization reference element; an optical sensor unit comprising a camera may be used to transmit 3D scan data, scanning extrinsic parameter data, and registration extrinsic parameter data; a common computing unit may be used to generate scanning extrinsic parameters and registration extrinsic parameters. For example, the 3D scanning system may comprise a camera used to detect structured light reflections off of the scanning surface (i.e. 3D scan data) and provide images of a tracker fixed to the anatomy (i.e. scanning extrinsic parameters with respect to the scanning reference element). Structured light, when projected on to the surface illuminates sections of the anatomy and reflects off of the surface. A computing unit may receive the 3D scan data comprising images captured (e.g. light is measured) from these reflections and receive scanning extrinsic parameters to generate a 3D surface scan. The same camera may be communicatively coupled to the same computing unit to generate images of the same tracker, while the tracker is in the same fixed position. The images are used to generate registration extrinsic parameters to register the 3D surface scan to the localization system. The computing unit may calculate a relative transformation between the registration extrinsic parameters and the tracker, the tracker serving as the localization reference element. The camera may then detect optical signals from an additional navigation tracker attached to a surgical tool. The optical signals provide navigation pose data to the computing unit which generates navigational information of the pose of the navigation tracker with respect to the 3D surface scan.

Alternatively, the localization system may be independent of the 3D scanning system and may use a different modality of operation.

Figure 2E:
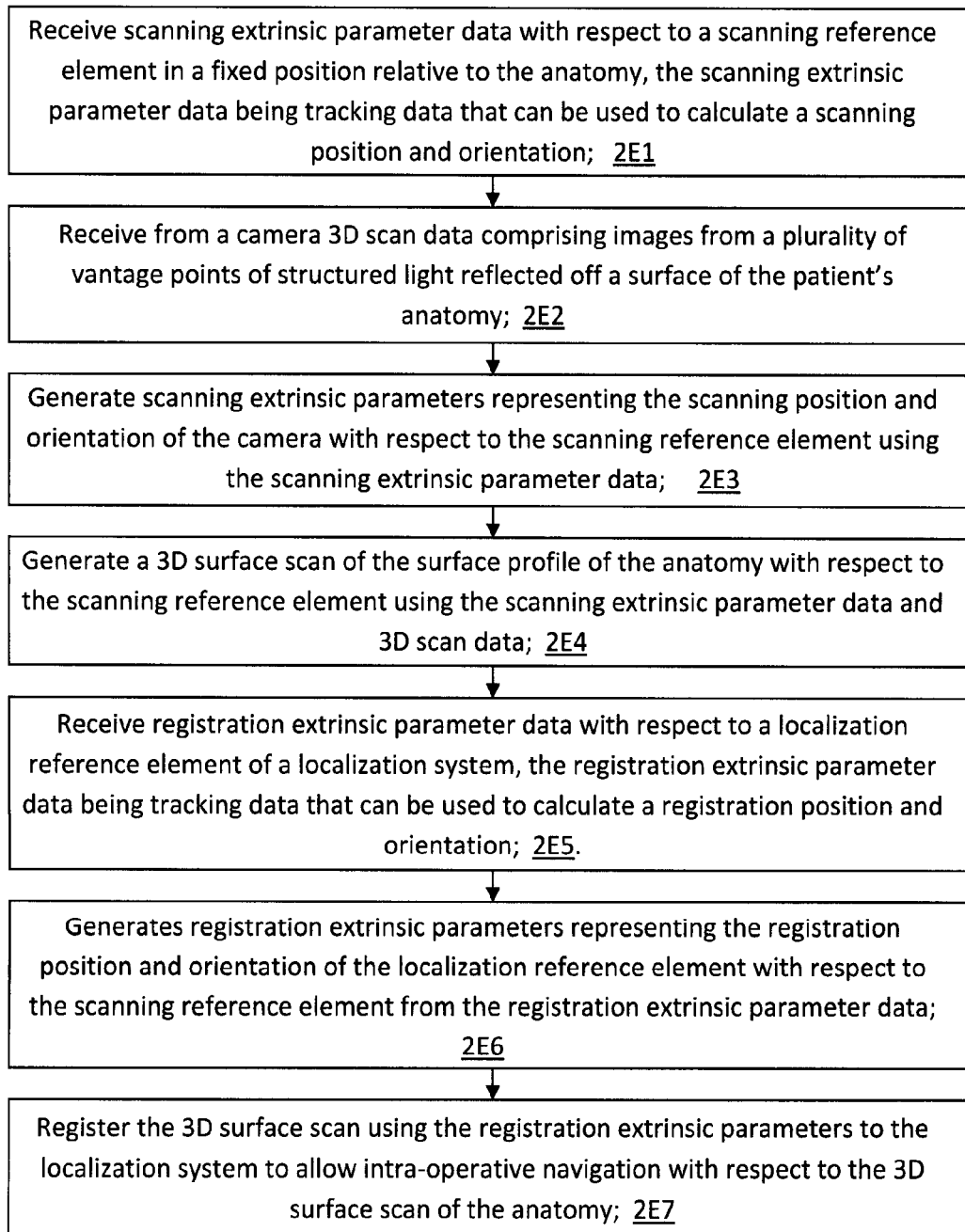
FIGS. 2E and 2F are flowcharts depicting computer implemented methods of modules of FIG. 2A (which may be adapted, as may be necessary, for similar modules of FIGS. 2B-2D.
Figure 2F:
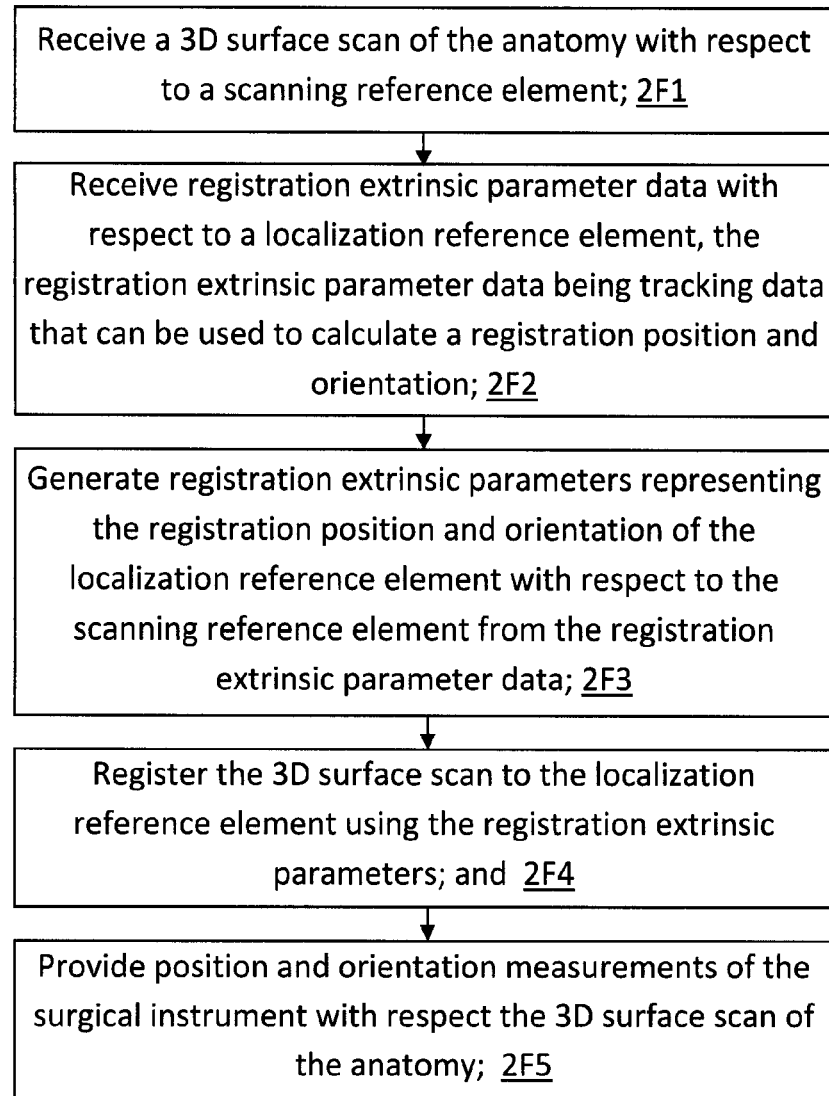

Referring now to FIGS. 2E and 2F, there are flowcharts that illustrate computer implemented methods. These methods may be operations or steps of modules 210, 220 and 230 described above.

FIG. 2E illustrates the operations of modules 210 and 220. At step 2E1, the computing unit (e.g. one or more processors) receives scanning extrinsic parameter data with respect to a scanning reference element in a fixed position relative to the anatomy, the scanning extrinsic parameter data being tracking data that can be used to calculate a scanning position and orientation. At step 2E2, the computing unit receives from a camera 3D scan data comprising images from a plurality of vantage points of structured light reflected off a surface of the patient's anatomy. At step 2E3, the computing unit generates scanning extrinsic parameters representing the scanning position and orientation of the camera with respect to the scanning reference element using the scanning extrinsic parameter data. At step 2E4, the computing unit generates a 3D surface scan of the surface profile of the anatomy with respect to the scanning reference element using the scanning extrinsic parameter data and 3D scan data. At step 2E5, the computing unit receives registration extrinsic parameter data with respect to a localization reference element of a localization system, the registration extrinsic parameter data being tracking data that can be used to calculate a registration position and orientation. At step 2E6, the computing unit generates registration extrinsic parameters representing the registration position and orientation of the localization reference element with respect to the scanning reference element from the registration extrinsic parameter data. At step 2E7, the computing unit registers the 3D surface scan using the registration extrinsic parameters to the localization system to allow intra-operative navigation with respect to the 3D surface scan of the anatomy.

FIG. 2F illustrates the steps of modules 220 and 230. At step 2F1, the computing unit receives a 3D surface scan of the anatomy with respect to a scanning reference element. At step 2F2, the computing unit receives registration extrinsic parameter data with respect to a localization reference element, the registration extrinsic parameter data being tracking data that can be used to calculate a registration position and orientation. At step 2F3, the computing unit generates registration extrinsic parameters representing the registration position and orientation of the localization reference element with respect to the scanning reference element from the registration extrinsic parameter data. At step 2F4, the computing unit registers the 3D surface scan to the localization reference element using the registration extrinsic parameters; and at step 2F5, the computing unit provides position and orientation measurements of the surgical instrument with respect the 3D surface scan of the anatomy.

Some additional considerations to maintain extrinsic parameter tracking during 3D scanning are described herein. When optical tracking is used, the system may provide a redundant tracking modality to avoid line of sight disruptions. For example, inertial tracking may be used which is tolerant of temporary line-of-sight disruptions. Using optical tracking, it is preferable to have a tracker that can be tracked from the variety of vantage points covering the desired surface profile. Redundant trackers may be provided such that if one tracker is occluded, a second tracker may still provide relevant tracking information. If a tracker mount to attach the reference element is in close proximity to the surface being scanned, with the mount being oriented such that it is substantially perpendicular to a face of the surface being scanned. This enables simultaneous tracking of the tracker and scanning of the scanning surface. Alternatively, a structured light projector that projects structured light may be attached to a tracker, while the camera may be rigidly fixed relative to the anatomy. One or more cameras may be used for scanning and/or localization.

As shown in module 240, it may be desirable to use the localization system further to provide navigation with respect to a medical image (e.g. a 3D medical image obtained from a CT or MRI), or with respect to an anatomical model. The digital medical image or model may be accessible in memory of the computing unit of the localization system for image registration. Image registration may involve two steps: a coarse registration, and a fine registration as described below. The resulting registration between the localization system coordinate frame, the patient's anatomy, and the medical image and 3D surface scan has high accuracy.

A method of coarse registration between a medical image and the anatomy may be performed by receiving input in the computing unit of the localization system to identify gross anatomical landmarks on the anatomy in the localization system coordinate frame; receiving input to identify locations on the medical image corresponding to the anatomical landmarks in the image coordinate frame; determining a transformation to map the anatomical landmarks to the identified locations in the respective coordinate systems. Steps to perform a fine registration may follow, in which the 3D surface scan is also registered to the localization system coordinate frame. Additional computations may be performed by the localization system using an initial guess of registration; at least in part to determine a transformation that aligns the medical image data and 3D surface scan with higher accuracy. For example, the computations may be an optimization operation such as iterative close point (ICP), where Euclidean distance between identified points on the medical image and the 3D surface scan is minimized, using the coarse registration to define an initial condition for the optimization operation.

Based on localization system registration, and optionally image registration, intra-operative localization provides real-time pose of a navigated object (such as the probe of FIG. 1) with respect to the patient's anatomy as represented by the 3D surface scan and/or medical images of the patient's anatomy.

Navigation pose data is provided to the computing unit of the localization system to calculate the pose of a navigated object in the localization system coordinate frame. The computing unit calculates the pose of a navigated object with respect to the 3D surface scan $T_O^S$, as follows: $T_O^S = T_L^S T_O^L$ where $T_O^L$ is a pose of the object with respect to the localization system coordinate frame and $T_L^S$ is a pose between the 3D surface scan and the localization system coordinate frame. Alternatively, where $T_S^M$ is a transformation between the medical image and the 3D surface scan, a current pose of the navigated object may be calculated as $T_O^M = T_S^M T_O^S$. The current pose of the navigated object with respect to the 3D surface scan and/or medical image may be communicated either to a user (e.g. via a display unit) or for further processing (e.g. to a robotic control system) to aid in delivering accurate therapy to a patient.

Figure 3:
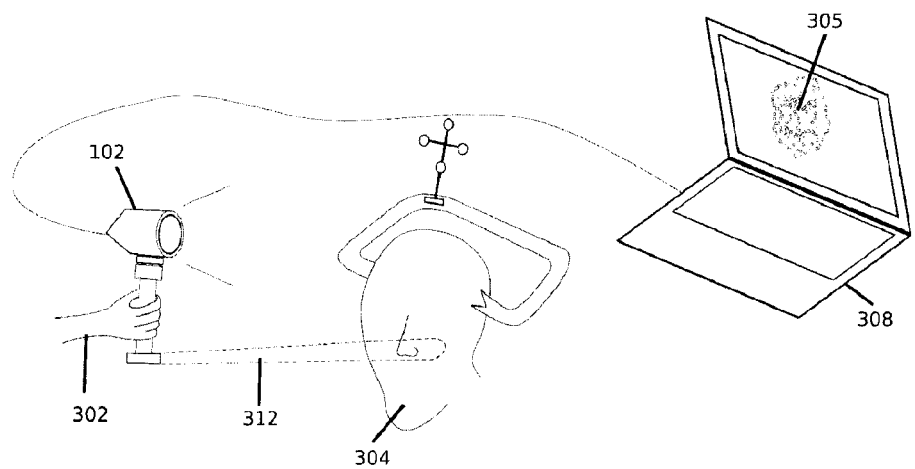
FIG. 3 depicts visual feedback provided to a user on a display unit.

Real-time visual feedback may be provided to a user on a display unit while scanning the patient's anatomy to generate a 3D surface scan. The visual feedback may include a graphic representation of the current 3D surface scan as it is being generated. The computing unit may enable the user to interact with the graphic representation such that the user may provide inputs to enhance viewing capabilities such as, panning, tilting, scaling, etc. This is illustrated in FIG. 3, where a user (user's hand 302 shown) is scanning a patient's face 304 (patient's body not shown), and a partially complete 3D scan 305 is shown on the display unit of a laptop computer 308. The scanning apparatus comprises a structured light projector 310 (projecting structured light 312) and a camera 102. The visual representation on the computing unit may indicate to a user the areas on the patient's anatomy that require further scanning thus providing guidance on spatial coverage of the anatomy.

Figure 4:
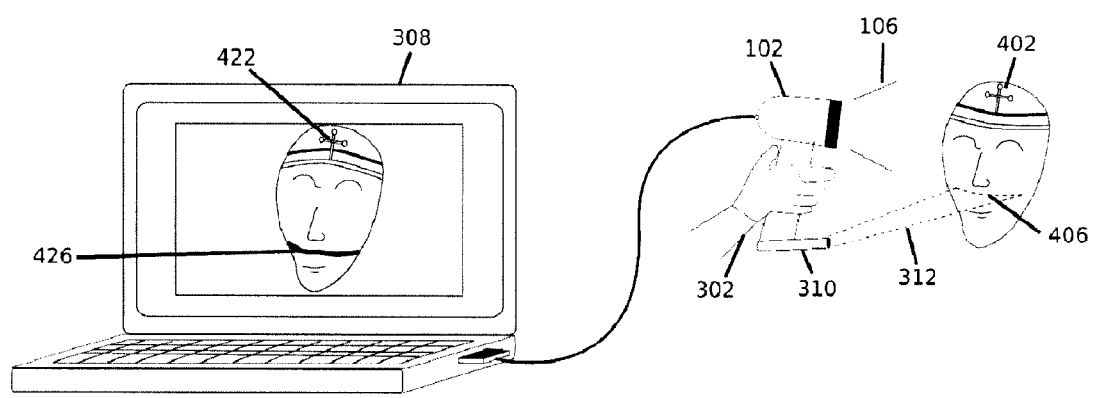
FIG. 4 shows a graphical representation on a GUI while a patient's head is being scanned with the 3D scanning system.

Referring now to FIG. 4, there is illustrated real-time graphical feedback provided to the user in the form of a camera feed on a display unit of a laptop computer 308 showing objects that fall within a field of view 106 of the camera. The camera feed of the 3D scanning system is displayed on a display unit, depicted as the display of an exemplary laptop computer in this figure. Displaying the camera feed to the user in real-time allows the user to view the field of view of the camera showing parts of the anatomy being scanned, images of the scanning reference element 422 (being the tracker 402) and/or the localization reference element, and/or images showing the reflections of structured light 426 off the patient's anatomy (corresponding to the location 406 where the light physically reflects on the patient's anatomy). It may be advantageous to visually emphasize features of the scanning reference element and/or the localization reference element (e.g. optically detectable markers of the respective trackers shown with a colored overlay) and the reflected structured light (e.g. a colored display of the reflected light). Visual feedback may be further modified to highlight the patient's anatomy (e.g. a colored overlay may be displayed to emphasize a part of the patient's anatomy that is reflecting the structured light).

The visual feedback provided to the user may also include modifications to the display of the tracker and/or markers that are partly based on quality metrics of current pose data (e.g. if a geometric error metric is exceeded, the markers may be shown with a yellow overlay, if a marker is occluded, no overlay is provided for that marker etc.).

Figure 5:
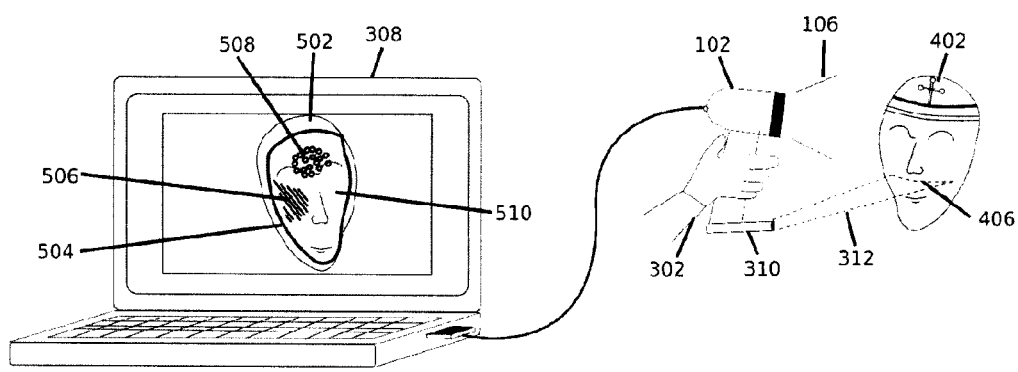
FIG. 5 shows a graphical representation on a GUI showing a medical image to guide 3D scanning.

The scanning system may use a 3D model (e.g. based on a 3D medical image) of the anatomy to display to a user on a display unit while the user is scanning the anatomy to generate a 3D surface scan. For example, a segmented 3D medical image of the patient's anatomy may be rendered and provided to the display unit. Reference is now made to FIG. 5. Anatomical features and/or surfaces of the anatomy required for a desired 3D scan are included in a view of the 3D model 502. If a single view cannot contain the required anatomical features and/or surfaces, then multiple views of the 3D model from perspectives that include the required anatomical features and/or surfaces may be displayed. On the view of the 3D model, the area that is to be registered using fine registration is visually identified. For example, a boundary on the surface of the patient shown as a scanning boundary 504 may be displayed to help guide the user. Additionally, the display of parts of the surface shown as surface A 506, surface B 508, and surface C 510 on the patient's anatomy may be modified to reflect a scanning status. For example, regions on the surface may appear visually distinct based on their scanning status. For example, surface A may be green reflecting a fully scanned region; a surface or region that is partially scanned (e.g. the scan density is insufficient) may appear as yellow (e.g. surface B); a surface that has not been scanned yet may appear as red (e.g. surface C). The appearance of the surfaces may modify in real time based on a coarse localization system registration, scanning extrinsic parameters, and optionally 3D scan data.

The system may display visual feedback via a display unit during 3D scanning. The display may include a visual representation of the 3D scan data, relative to Registration Data Criteria. Registration data criteria are criteria based on 3D scan data that are a metric of the completeness of the 3D scan and/or readiness of the 3D scan for use in registration. These criteria may include: correlation of aggregate 3D scan data with expected surface profile (e.g. via medical image accessible in memory); spatial and/or angular coverage of 3D Scan Data with respect to anatomy; density of 3D Scan Data with respect to anatomy; etc. The visual feedback may incorporate a 3D visualization of the patient's anatomy, via a standard model or via a medical image. The visual feedback may further include progress bars, or other such indicators, for various metrics relating to the Registration Data Criteria. The system (via instructions executing on computing unit) may determine when sufficient 3D scanning data has been collected, and auto-complete the step, and transition the display to the next step in the software workflow. For example, the system may determine that sufficient 3D scanning data has been collected based on Registration Data Criteria (described above) and proceed to a next step in a workflow.

Figure 6:
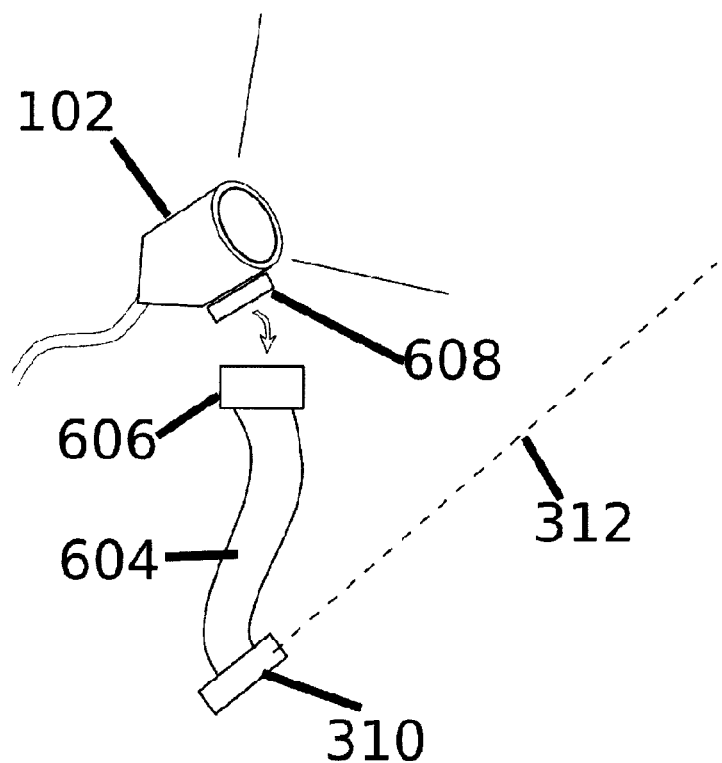
FIG. 6 illustrates a 3D scanning system comprising a camera, communicatively coupled to a computing unit, and a structured light projector shown here on a handle.

To further illustrate a 3D scanning system disclosed herein, reference is now made to FIG. 6. This figure illustrates a structured light projector 310 that is removably attached to a camera 102, the camera being communicatively coupled to a computing unit (not shown). The structured light projector 310 and camera 102 are assembled into an assembly that is configured to be handheld by a user. When attached, a field of view of the camera 102 overlaps with the projected structured light (e.g. represented by broken line 312). A handle 604 is configured to allow a user's hand to grasp the assembly and point the assembly at a patient's anatomy. The handle has a mounting mechanism 606. The camera may be removably attached using a camera attachment mechanism 608. The camera may further be used for intra-operative localization as part of a localization system. As discussed previously, the localization system and 3D scanning system may share the same hardware or may be distinct systems. The attachment mechanism used in the camera mounting location may be a magnetic kinematic mount, a cam lock, a dove-tail connection, or any other mechanical attachment mechanism. The removable attachment mechanism may allow repeatable and precise attachment, such as a kinematic mount. When the attachment is repeatable, it may be possible to preserve a co-registration between the structured light projector and the camera such that the camera and structured light projector can be used while in a known positional relationship with respect to each other. During a navigation procedure, this may be useful to a user to attach and detach the camera at different stages of a workflow as needed. The removable attachment mechanism may be repeatable to enable a fixed and known co-registration between the camera and the structured light projector, thus removing a need to calibrate the structured light projector with respect to the camera.

Figure 7:
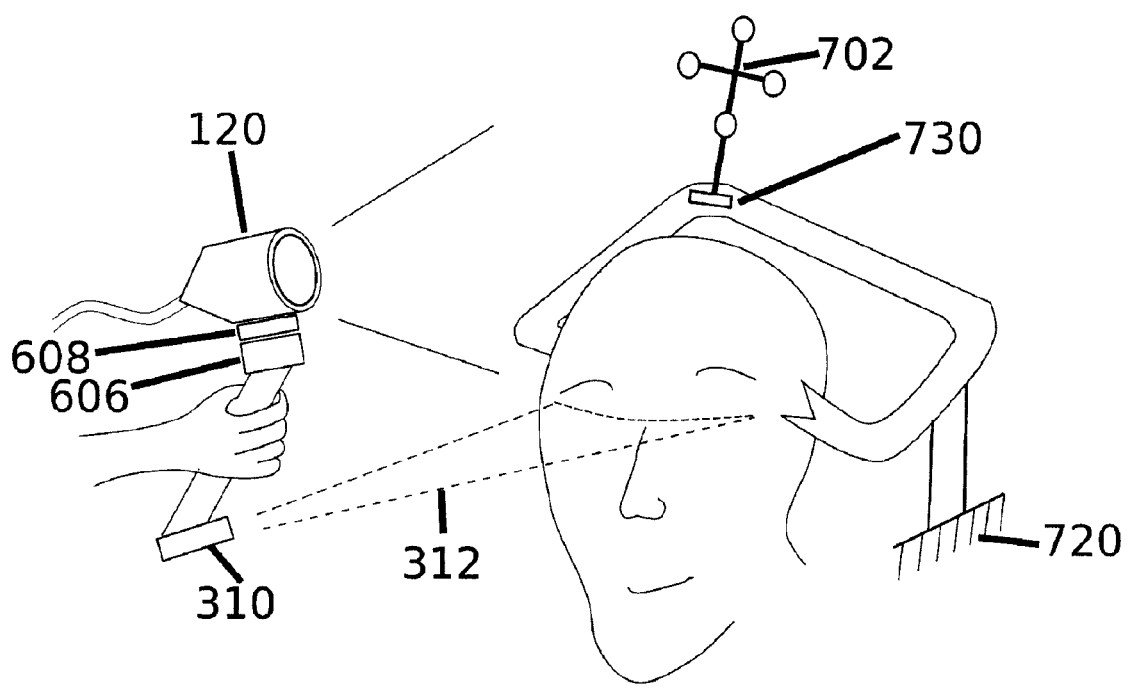
FIG. 7 depicts the 3D scanning system in use to generate a 3D surface scan on a patient's head.

Reference is now made to FIG. 7. The user grasps the handle and points the assembly at the anatomy to be scanned. As shown here, the anatomy is a patient's head that is immobilized using a head clamp (i.e. fixed in space, as indicated through the connection to the ground symbol 720). The structured light reflects off of the head. The field of view of the camera shows the reflected structured light, and optionally a tracker having a fixed position relative to the anatomy. The tracker may be releasably and repeatably attached with respect to the anatomy. In this illustration, the camera is being used to generate scanning extrinsic parameter data using the tracker 702 (mounted to mounting location 730) as the scanning reference element.

Figure 8:
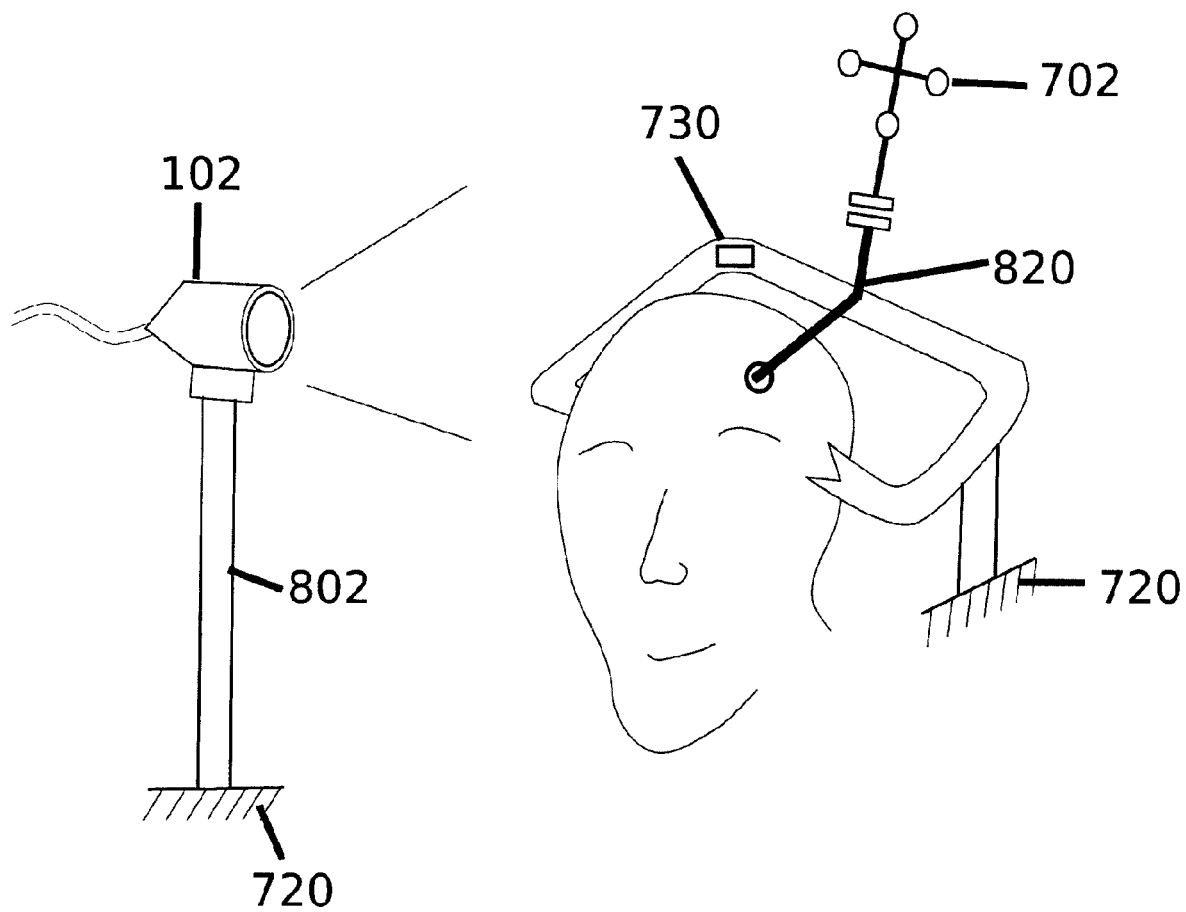
FIG. 8 illustrates the camera of the 3D scanning system in use as part of a localization system to provide intra-operative navigation with respect of the 3D surface scan of the patient's head.

Reference is now made to FIG. 8. This figure illustrates shared hardware between the scanning system and the localization system. The camera is used for 3D scanning and intra-operative localization. Upon generation of the 3D surface scan, the camera can be removed from the handle, and attached to a camera mount 802 having a fixed position in space. When attached to the camera mount, the camera can be aimed at the surgical site such that it can detect the tracker (while still attached in the same position as when used as scanning reference element) to generate registration extrinsic parameter data that can be used to register the 3D surface scan to the localization system. In FIG. 8, the camera mount is shown to have a fixed positional relationship with the anatomy (i.e. the camera may be the localization reference element), and the tracker 702 is shown mounted to a tool 820 for intra-operative localization.

If the camera is utilized as the localization reference element, the tracker, if releasably attached to the anatomy, may be released and attached to a surgical instrument for intra-operative localization/navigation after generation of the registration extrinsic parameters. Alternatively, if the tracker remains in a fixed positional relationship to the anatomy during intra-operative localization, the tracker may be the localization reference element and the camera may not be required to remain in a fixed position relative to the anatomy.

Figure 9A:
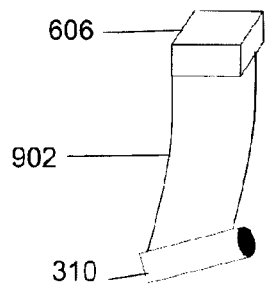
FIG. 9A depicts a handle with a camera mounting location and the structured light projector.

Reference is now made to FIG. 9A which depicts a structured light projector 310 on a handle 902. On a first end of the handle, the mounting location 606 may have a mechanism configured to rigidly and releasably mount the camera. Example mechanisms include kinematic mounts, screw locks, cam locks, dovetail connections, etc. On a second end, there may be a structured light projector, the projector being configured to project structured light (e.g. a pattern of light). The handle may be configured to be ergonomically grasped by a user and may comprise a human machine interface (e.g. a button) to provide inputs to the computing unit of the scanning system. The general positional configuration of the camera, the projector and the handle may be such that when grasped by a user, the field of view of the camera and the structured light projector point generally outward (i.e. generally along the axis of the user's arm) and structured light is projected within the field of view of the camera.

It may be beneficial for the camera and structured light to be co-registered. For two components to be co-registered in this context, means that there is a known positional relationship between the two components. This positional relationship may be obtained by using known geometrical attributes of the handle, camera and structured light projector. In the configuration described above, the camera is communicatively coupled to a computing unit, has a known positional relationship (i.e. known to the computing unit) between the camera coordinate system and the structured light projector.

Alternatively, steps to co-register the camera and the structured light projector may be carried out in a co-registration process. The process may be carried out in a manufacturing facility or by an end user.

Figure 9B:
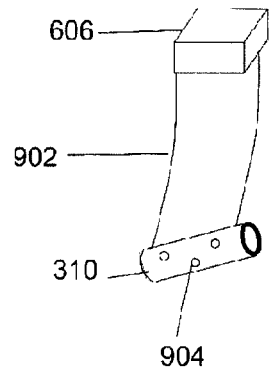
FIG. 9B depicts the handle with calibration divots.

Referring now to FIG. 9B which shows a handle configured for a co-registration process by providing mechanical calibration features 904 having a known positional relationship to the structured light. As illustrated in this Figure, the mechanical features are three divots. The divots may be localized by an external localization system or by using the camera of the scanning system to localize a tip of a probe (i.e. the probe having a tracker attached thereto), and bringing the tip of the probe in contact with the divots. The computing unit in communication with the camera receives image data corresponding to the divots with respect to the camera to compute a measured relationship between the divots and the structured light projector. Further, the computing unit accesses a known spatial relationship between the divots and the structured light projector. Using the known spatial relationship between the divots and the structured light projector, and the measured spatial relationship between the divots and the camera, the computing unit determines a co-registration i.e. a positional relationship between the camera and the structured light projector.

Figure 9C:
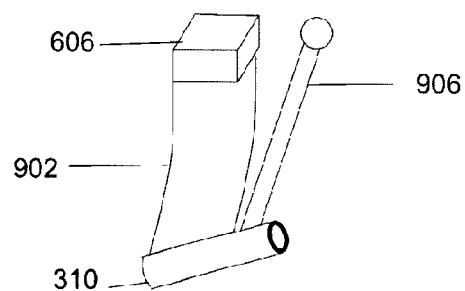
FIG. 9C depicts the handle with an optically detectable feature.

Reference is now made to FIG. 9C. As illustrated, the co-registration may be determined or verified by providing at least one optically detectable feature 906 having a known positional relationship with the structured light projector, and configured to be within the camera's field of view when the camera is attached to the handle. The computing unit receives optical data corresponding to the optically detectable feature, accesses the known spatial relationship between the optically detectable feature and the structured light projector, and either a) determines the co-registration between the camera and the structured light projector, or b) determines an expected position of the optically detectable feature based on an expected co-registration, and compares the expected location to the detected location to generate a verification metric. The verification metric may indicate whether the structured light projector is co-registered to the camera, and may be provided to further computational steps and/or guidance to a user via a display unit.

Figure 9D:
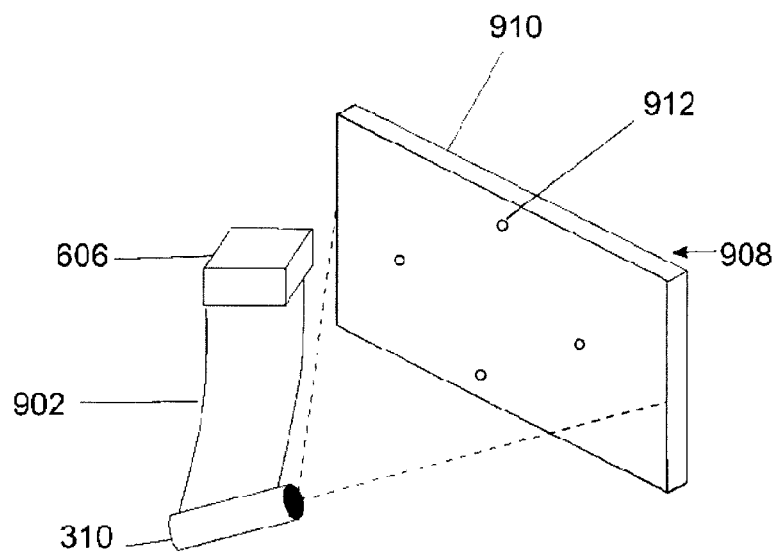
FIG. 9D depicts a characterization jig with optically detectable features.

Reference is now made to FIG. 9D. A characterization jig 908 may also be used to enable the computing unit to compute the co-registration. The characterization jig has a reference surface 910 and optically detectable features 912. The spatial relationship and characteristics of the reference surface and the optically detectable features are known to the computing unit (e.g. accessible in memory). The computing unit is configured to calculate a pose of the characterization jig. The computing unit is further configured to generate 3D scan data of the reference surface. The reference surface is scanned (e.g. by a user). The computing unit determines the co-registration based on the 3D scan data, the pose and the known spatial relationship and characteristics of the characterization jig. A tracker may be used as the characterization jig with the reference surface being a geometrical shape of a body of the tracker and the optically detectable features of the tracker being optically detectable features of the characterization jig.

Alternatively, a system may implement a method of verifying or determining a co-registration while scanning a surface to generate a 3D surface scan. In this case, 3D scan data (e.g. reflected light off of the object being scanned), along with scanning extrinsic parameters are received by the computing unit. The computing unit receives sufficient scanning extrinsic parameters data and 3D scan data to execute computations to verify and/or calculate the co-registration. Computations of this nature are known in the art of Simultaneous Localization and Mapping. Such 3D scan data may comprise a more complex pattern of light, since a more complex pattern contains additional information and helps provide more data to the computing unit to verify or calculate the co-registration. Examples of more complex patterns as projected on to a surface include: checkerboard, crosshair, dot matrix, line, parallel line, circle, concentric circles, etc.

In another method of determining the co-registration, the structured light is reflected off a known surface profile (e.g. a flat surface). Without the need for any scanning extrinsic parameter data, the computing unit may calculate and/or verify the co-registration using the reflections of the structured light and the known surface profile. To enable this, it may be advantageous to project a more complex pattern (examples of which are provided above), such that the co-registration between the structured light projector and the camera may be determined.

Figure 9E:
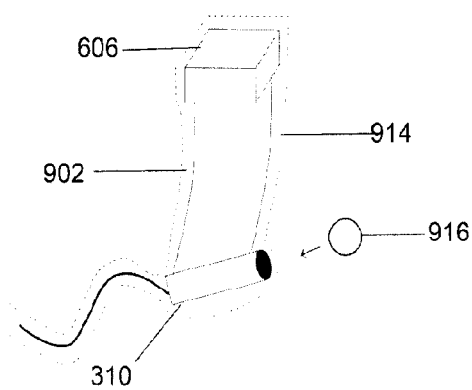
FIG. 9E depicts the handle covered in a sterile drape.

Reference is now made to FIG. 9E. Where the assembly of the structured light projector and handle is used within a surgical sterile field, it may be enclosed within a sterile drape 914, the sterile drape 914 having features that facilitate attachment of the camera to the camera mounting location, and allow undistorted transmission of structured light (e.g. a clear thin drape with an elastic band 916 to hold the drape taut over the structured light aperture). Other methods of maintaining sterility are also contemplated, such as: autoclavable; single-use disposable, pre-sterilized; etc.

The following examples in FIGS. 10-13 describe a camera being used as shared hardware between a localization system and a scanning system. These examples are not meant to be limiting and it is understood and described below that an external localization system using a different modality (e.g. electromagnetic, optical etc.) and/or different hardware components (e.g. camera, computing unit etc.) may be used to obtain similar results.

Figure 10:
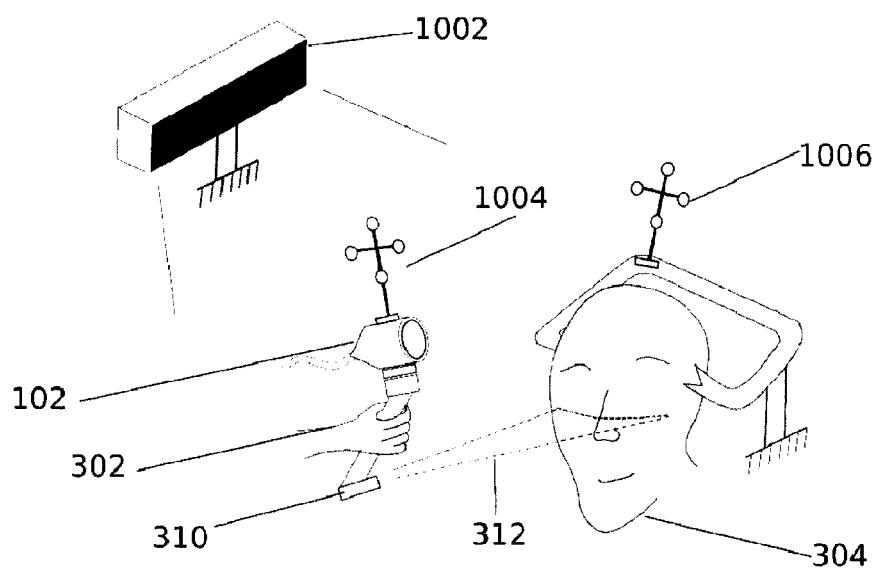
FIG. 10 depicts an external localizer system localizing targets on the camera and the patient's anatomy.

Navigation/localization systems that do not utilize the hardware of the surface scanning system may be used for intra-operative localization. Reference is now made to FIG. 10. An external localization system (depicted as a stereo camera 1002 fixed to an arbitrary location within a room) may be used for intra-operative localization. Localization systems using a different modality than optical are also contemplated. To enable 3D surface scanning, a 3D surface scanning system is depicted as a handle 902, a camera 102 with a structured light projector 310. The 3D surface scanning system generates 3D scan data (e.g. via the structured light reflections measured by the optical camera) and optionally scanning extrinsic parameters (e.g. via a tracker mounted in a fixed location relative to the anatomy, and visible to the camera while scanning). Alternatively, the scanning extrinsic parameter data may be measured by the external localization system and communicated to the 3D scanning system. Any means for generating 3D scan data and/or scanning extrinsic parameters is contemplated; the elements in the figure are exemplary.

To perform a localization system registration, registration extrinsic parameters are generated. For example, as shown in FIG. 10, the registration extrinsic parameters may be determined by tracking a first tracker 1004 attached to the scanning system, and, optionally, a second tracker 1006 attached to the anatomy. The first tracker may have a known positional relationship with respect to the camera's coordinate frame in which case, a second tracker may not be needed for generating registration extrinsic parameters, since the relationship between the 3D scan and the first tracker 1004 are known, and the 3D scan may be related to the localization system coordinate frame. Where the scanning system and intra-operative localization system are separate, the computational steps may be distributed among the computational hardware of the respective systems.

The next part of this specification describes in detail various applications of the scanning system and the localization system in the context of different surgical procedures e.g. knee, cranial and ENT procedures. Similar to the description above, it is to be understood that the scanning system and localization system may be implemented on the same physical hardware or may be implemented as distinct systems.

Figure 11A:
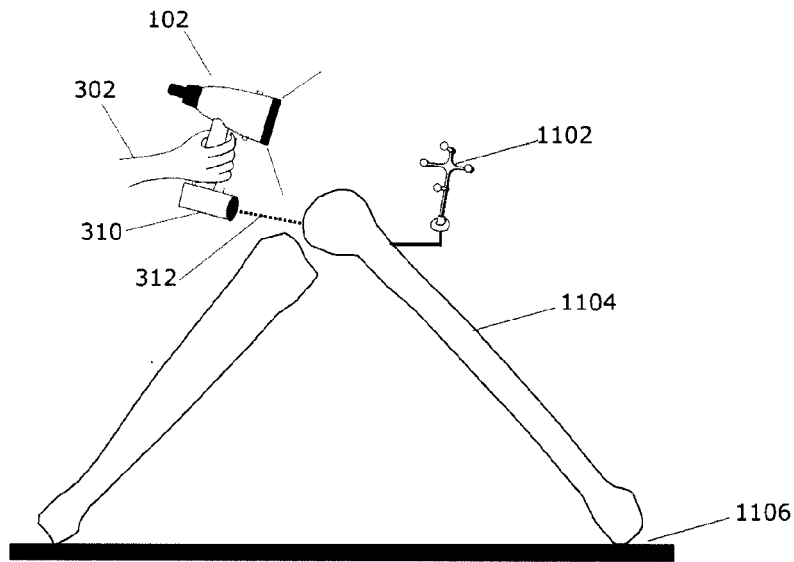
FIGS. 11A, 11B and 11C show use of the 3D scanning system in a knee replacement procedure.
Figure 11B:
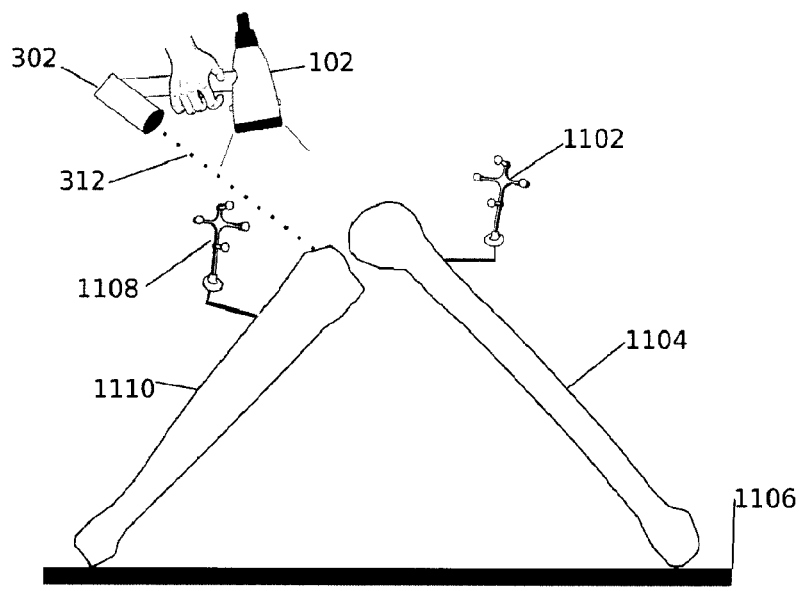

In one exemplary application, use of a system for 3D surface scanning and intra-operative localization is shown in the context of knee replacement surgery on a patient. Reference may be made to FIG. 2C as well as to FIGS. 11A, 11B and 11C. A 3D surface scanning system comprising a camera 102 and a structured light projector 310 is shown. A method comprising user and computer implemented steps to enable intra-operative localization is described below:

1. A pre-operative image or model of the knee, comprising a model for a distal femur and/or an other model for a proximal tibia, is optionally loaded into the computing unit.
2. A patient's knee is prepared and exposed.
3. As shown in FIG. 11A, a first tracker 1102 is attached to a femur 1104 (only bones shown in the figure for clarity) as the patient is lying on an operating table 1106.
4. An assembly of a camera and a structured light projector, the camera being connected to a computing unit (not shown) is used to scan the distal femur of a knee. Reflections of the structured light off of the distal knee and scanning extrinsic parameter data using the first tracker are received by the camera. The assembly is moved to a plurality of vantage points such that the surface of the distal femur is scanned to a sufficient density and/or spatial coverage.
5. A 3D surface scan of the distal femur is generated by a computing unit. Optionally, a pre-operative image or model is used to facilitate the generation of the 3D surface scan and/or enhance the scan as described previously in the application.
6. As shown in FIG. 11B, a second tracker 1108 is attached to the tibia 1110.
7. The assembly scans the proximal tibia and a 3D scan of the proximal tibia is generated, optionally making use of the pre-operative image or model.
8. Further computations are carried out by the computing unit to condition the 3D scan data for use in intra-operative navigation. Such computations described in this specification may include:
    i. Image registration;
    ii. Image segmentation and/or disturbance rejection;
    iii. Noise filtering; and/or
    iv. Kinematic analyses and/or simulations based on the knee geometry.
9. If removably attached, the camera and/or structured light projector may be detached from the handle. The structured light projector may be set aside for the remainder of the surgical procedure.

Figure 11C:
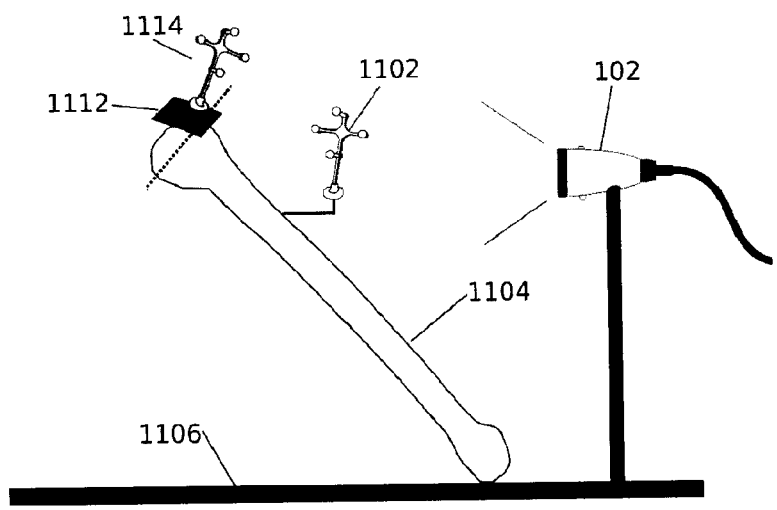

10. As shown in FIG. 11C, the camera is then mounted for intra-operative localization, for example, on a mounting location on an operating table 1106.
11. Registration extrinsic parameters are generated from registration extrinsic parameter data. The registration extrinsic parameters are a pose between the tracker attached to the femur and the camera. The same femur tracker is both the scanning reference element and the localization reference element. The femur tracker remains attached to the femur in the same position during scanning and localization. The computing unit can register the 3D surface scan to the localization system.
12. Registration extrinsic parameters required for localization system registration to register the tibia bone are a pose between the tibia tracker and the camera.
13. With 3D scans of both bones registered to the localization system, intra-operative localization is enabled. For example, in FIG. 11C, a cutting guide 1112 is depicted with a navigation tracker 1114 attached to it; the localization system may provide the surgeon with relevant information about the position and orientation of the cutting guide relative to the femoral anatomy (based on the 3D surface scan of the distal femur).

A 3D surface scanning system such as shown in FIG. 2E may also be used for a minimally invasive cranial/neurosurgical application. A surgeon may desire to access a location within a patient's brain (e.g. tumor, lesion) that has been identified on a medical image, such as an Mill. The following are exemplary steps describe a method to enable intra-operative localization:

1. Patient is prepared and positioned for surgery. The patient's head may be rigidly fixed within a head clamp (as shown in FIG. 1)).
2. Prior to establishing a sterile field, a 3D surface scanning system (as shown in FIG. 7) may be used to generate a 3D surface scan. The camera has a structured light projector attached thereto, and a tracker releasably attached to the head clamp (directly, or via a fixable articulating arm, as is used in some existing cranial navigation procedures) is used to generate scanning extrinsic parameters. The camera is communicatively coupled to a computing unit.
3. After generation of the 3D surface scan, and prior to establishing a sterile field, the camera is attached to a camera mount with a fixed positional relationship to the tracker (as shown in FIG. 8). The camera mounting location may be attached directly to the head clamp, e.g. via a lockable articulating arm. The camera is attached such that its field of view encompasses the surgical site as well as the tracker, when attached to the head clamp.
4. Prior to establishing the sterile field, with the camera mounted to the camera mount and the tracker mounted to the head clamp, registration extrinsic parameter data is received and registration extrinsic parameters are generated (i.e. the pose of the tracker with respect to the camera is computed by the computing unit). This pose is used to register the 3D surface scan to the localization system coordinate frame.
5. The sterile field is then established. The tracker may be removed from the head clamp. The head is prepared and draped for sterility. The camera is draped with the camera remaining in its fixed position on the camera mount. The drape may comprise an optically transparent window that allows the camera to receive optical signals.
6. The computing unit generates an image registration to map a medical image (e.g. MRI) to the 3D surface scan, in accordance with steps described in this specification.
7. Once the 3D surface scan is registered to the camera and the medical image registered to the 3D surface scan, the system is capable of providing intra-operative localization with respect to the 3D surface scan and/or the medical image. A sterile tracker is attached to a surgeon's instrument (e.g. a probe used to localize a point within the brain), the sterile navigation tracker being localized such that the instrument's position relative to the medical image of the brain may be computed and displayed to a surgeon.

In an alternative application, non-sterile 3D surface scanning is carried out using the 3D scanning system, and the intra-operative localization is carried out by an existing intra-operative navigation system, e.g. Stealthstation® navigation system (Medtronic, Minneapolis, Minn.).

Figure 12A:
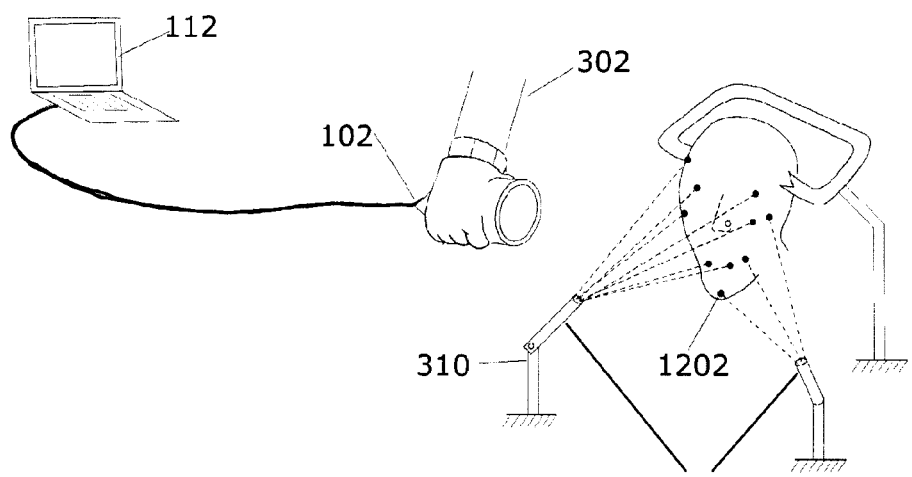
FIG. 12A depicts an external structured light projector of the 3D scanning system.

In another exemplary application illustrated in FIG. 12A, the 3D scanning system includes one or more structured light projectors (e.g. 1210 that have a fixed positional relationship with respect to a patient's anatomy (in FIG. 12A, the structured light projectors and head clamp are shown to have spatially fixed positions). The computing unit 112 connected to the handheld camera 102 may be used to receive 3D scan data (i.e. reflections of the structured light off of the anatomy, in this case a patient's head) and generate scanning extrinsic parameters. Alternatively, scanning extrinsic parameters of the camera 102 with respect to the anatomy may be determined from the structured light reflections as the structured light reflections act as fiducials 1202, having a fixed location with respect to the anatomy. The computing unit generates a 3D surface scan of the anatomy using the scanning extrinsic parameters and the 3D scan data. Multiple structured light projectors may be advantageous to increase the reflections of structured light off the anatomy being scanned, as well as to provide tolerance to occlusion of structured light from any one of the structured light projectors.

Figure 12B:
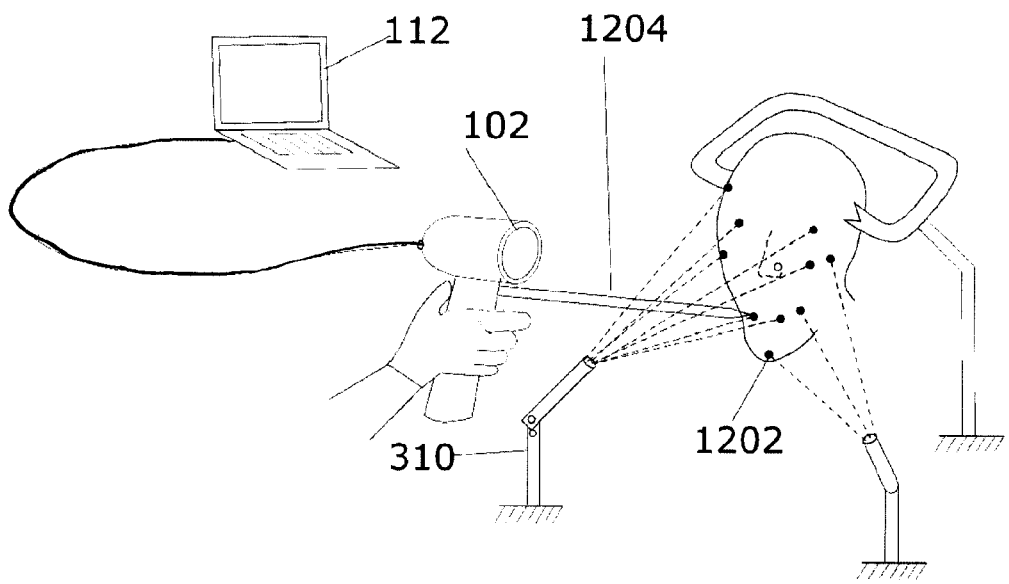
FIG. 12B illustrates the camera of the 3D scanning system being attached to a surgical instrument and used in intra-operative localization.

Reference is now made to FIG. 12B. Intra-operative localization may also be performed when the camera is attached to a surgical instrument 1204. The camera may provide detected structured light reflections to a computing unit for relative pose calculation of the 3D surface scan with the surgical instrument (thus enabling intra-operative localization).

Figure 13:
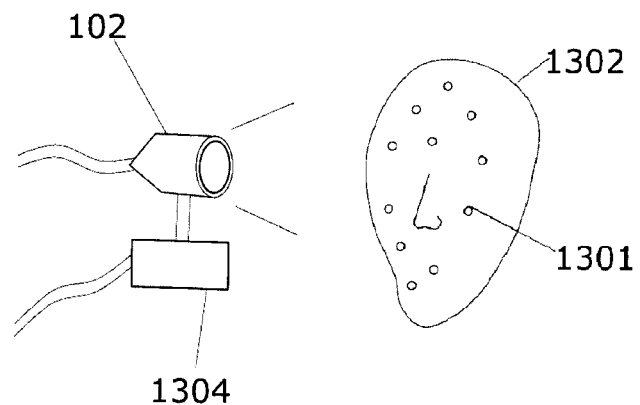
FIG. 13 depicts use of fiducials to generate scanning extrinsic parameter data.

Reference is now made to FIG. 13. It may also be possible that a multitude of optically detectable fiducial markers 1301 are affixed on a patient's face 1302 thereto (only specific features of the face shown). To generate a 3D surface scan, the fiducials are detected by the camera 102, which may be handheld by a user (not shown). Multiple vantage points of the patient's face are used to capture images of the patient's face including the fiducial markers. In a further variation and to illustrate the use of a different modality of tracking, the scanning system may be an Electro-Magnetic (EM) tracking system. An EM tracker 1304 is shown attached to the camera 102. Scanning extrinsic parameters may be generated by calculating pose data of the EM tracker. A computing unit (not shown) executes instructions to generate a 3D surface scan using images of the fiducials and the corresponding scanning extrinsic parameters. To register the 3D surface scan to the EM localization system, the EM tracker 1304 of FIG. 13 may also be attached to the camera 102 with a fixed and known pose between the camera coordinate system and the EM tracker coordinate system.

Figure 14:
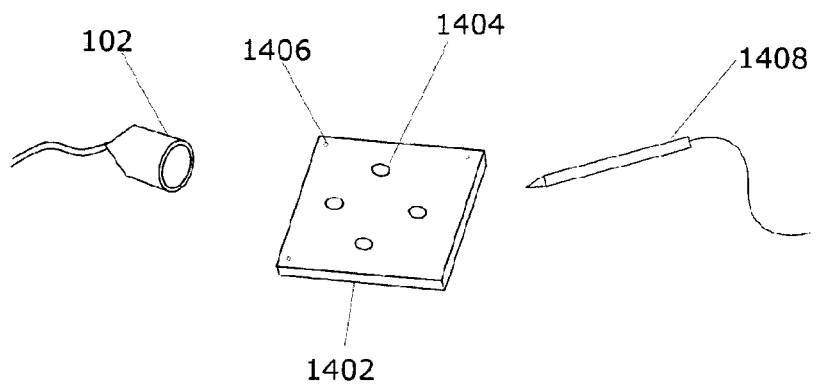
FIG. 14 illustrates use of a jib with an optical and electromagnetic modality.

Referring now to FIG. 14 which illustrates a registration jig 1402 that may be used in the alternative to register a 3D surface scan to an electromagnetic localizer system. An optical pose of the jig is generated with the camera 102 detecting optically detectable fiducials 1404 on the jig. While the jig is held stationary, a pose of the jig is obtained with the EM tracking system. The pose may be generated by probing one or more registration divots 1406 using a probe 1408 that can be tracked electromagnetically. The computing unit (not shown) receives camera data and probe data of the registration divots. Using a known relationship between the fiducials and the registration divots, the computing unit computes a first pose of the jig based on optical data, and computes a second pose based on the EM probe data. The relative pose as measured by the two systems is the registration between the camera (and thus, the 3D surface scan) and the localization system.

In another exemplary application, the 3D scanning system (for example, a camera and structured light projector) is integrated with a robotic surgery system. The 3D scanning system may be attached to or near an end effector of the robot instead of being handheld by a user in previous examples.

Typically, robotic surgery systems generate extrinsic parameters of the end effector with respect to the anatomy. These extrinsic parameters provided by the robotic system (e.g. via robot encoders, or by a localization system associated with the robot) may be utilized by the scanning system as scanning extrinsic parameters to aid in generating the 3D surface scan. This is advantageous, since it alleviates the need of the 3D scanning system to provide additional computer implemented methods and/or hardware to generate scanning extrinsic parameters. A computing unit of the robotic system may be communicatively coupled to a 3D scanning system to provide the scanning extrinsic parameters to the computing unit of the 3D scanning system for generating a 3D scan. The 3D surface scan may then be provided to the computing unit of the robotic system for further use in robotic surgery.

Alternatively, the scanning system may generate scanning extrinsic parameters via the camera and computing unit by localizing a tracker associated with the robot's localization system, the tracker being rigidly fixed to the anatomy being scanned. This is advantageous, since it leverages the existing hardware provided by the robotic system, and therefore alleviates the 3D scanning system's need to provide additional hardware to generate extrinsic parameters.

Figure 15A:
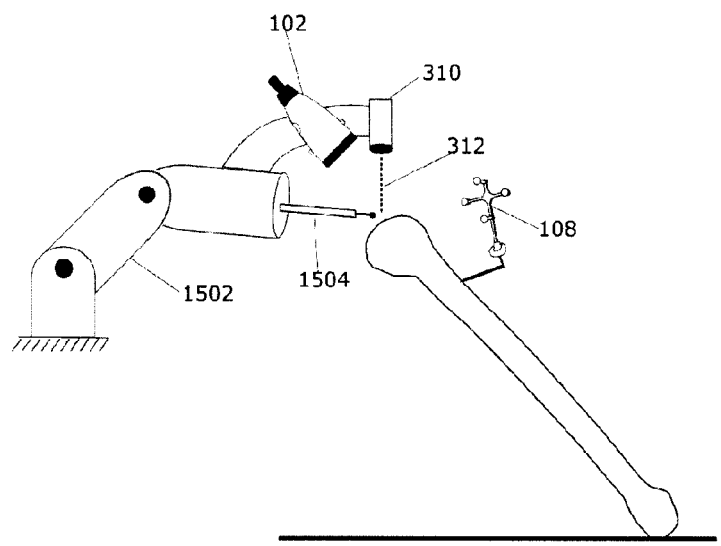
FIG. 15A shows the 3D scanning system in use with a robotic system and FIG. 15B shows a flowchart of a computer implemented method.
Figure 15B:
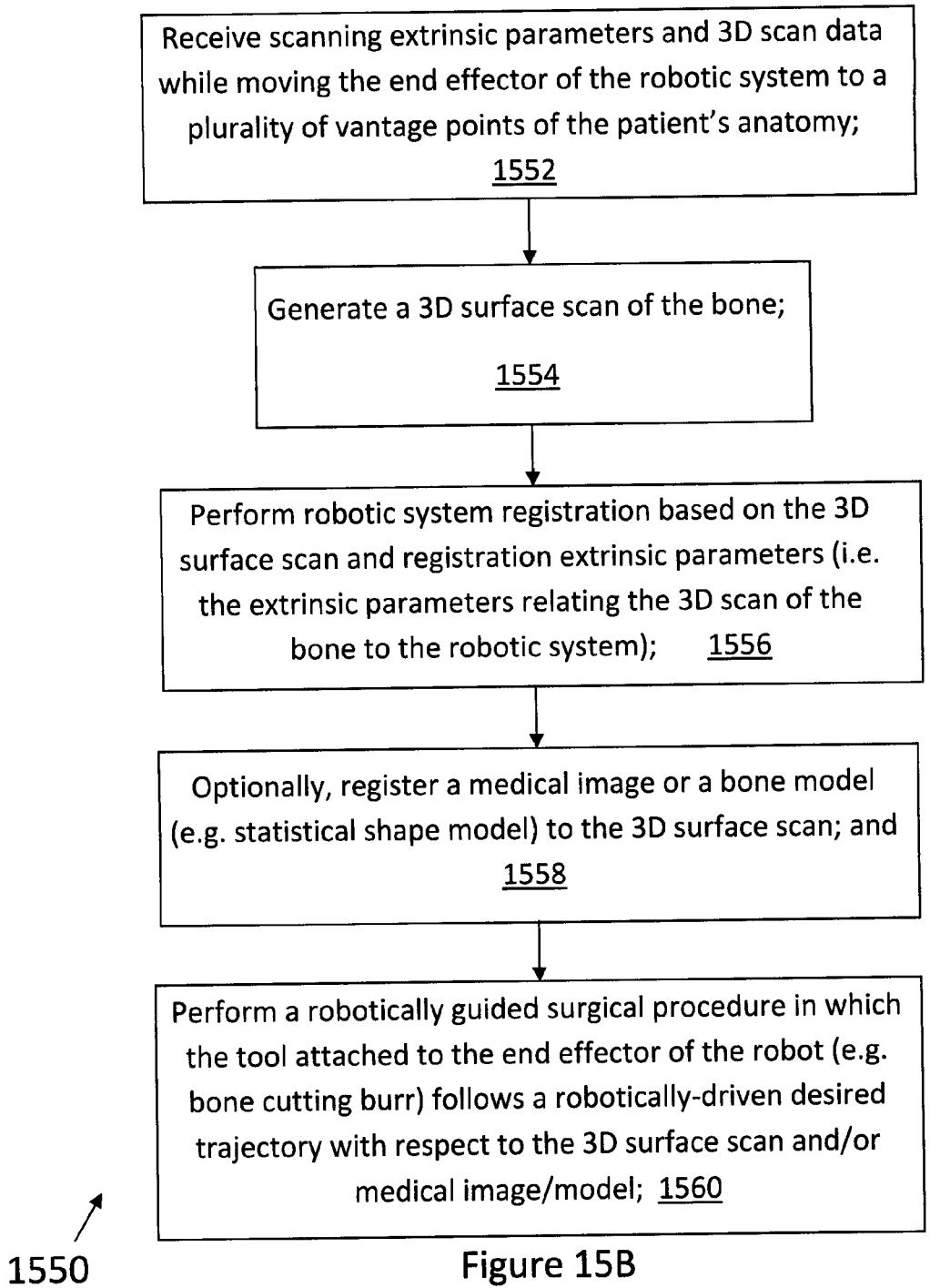

Referring now to FIG. 15A, the camera 102 and the structured light projector 310 are illustrated to be rigidly attached to an end effector of a robot 1502. The end effector is depicted to be a surgical burr tool 1504 for bone removal. The camera and structured light projector are configured to generate a 3D surface scan, as described previously in this specification. The tracker 108 is attached to the bone, and is exemplary of a means to generate extrinsic parameters required for 3D scanning. The scanning extrinsic parameters may be computed by using the camera 102 to localize the tracker 108, or by using another localization system. A computer implemented method of use 1550 may be illustrated in as follows:

Receive scanning extrinsic parameters and 3D scan data while moving the end effector of the robotic system to a plurality of vantage points of the patient's anatomy (1552);
Generate a 3D surface scan of the bone (1554);
Perform robotic system registration based on the 3D surface scan and registration extrinsic parameters (i.e. the extrinsic parameters relating the 3D scan of the bone to the robotic system) (1556);
Optionally, register a medical image or a bone model (e.g. statistical shape model) to the 3D surface scan (1558); and
Perform a robotically guided surgical procedure in which the tool attached to the end effector of the robot (e.g. bone cutting burr) follows a robotically-driven desired trajectory with respect to the 3D surface scan and/or medical image/model (1560).

Reference is now made to FIG. 16 illustrating components of a computer system 1600 including software modules stored as previously described. When a 3D scanning system is used with a robotic system, it may include additional operations to plan trajectories to ensure that sufficient or appropriate registration and/or 3D scan data is collected. For example, a Trajectory Planner is implemented as a real-time computational module 1602 that commands a particular trajectory of output poses of the end effector. Initially, this commanded trajectory may use an initial pose estimate (e.g. a starting guess or approximate registration) of a relative pose between the end effector of the robot and the anatomy to be registered. The Robot Control and Localization System 1604 is a closed loop dynamic system in which a pose of the end effector of the robot is both measured by the system, and effects the commanded trajectory. The output of the Robotic Control and Localization System is a pose of the end effector (i.e. a pose that is measured by the Robotic Control and Localization system). A 3D scanning system camera (e.g. 1606 and similar to as described above) may be attached to the robotic end-effector. The reflected structured light is used to generate 3D scan data. The 3D scan data and end effector pose (i.e. scanning extrinsic parameters) are provided to the 3D Surface Scan Generator Module 1608 (similar to module 210), to then generate the 3D scan.

The Trajectory Planning Module 1602 is programmed to update the commanded trajectory so that metrics associated with the 3D scan data and/or the end effector pose meet Registration Data Criteria. These criteria are used to determine suitability of the 3D scan data for an accurate registration of the 3D surface scan to the robotic system and optionally, to a medical image and/or anatomical model. For example, Registration Data Criteria may include: correlation of aggregate 3D scan data with an expected surface profile obtained from a medical image that is accessible in memory (e.g. using computational techniques described with respect to image registration); spatial and/or angular coverage obtained in the 3D scan data with respect to the anatomy; density of 3D scan data with respect to the anatomy etc.

The Trajectory Planning Module 1602 may receive a priori information about the anatomy (e.g. medical image of the anatomy such as, CT or MRI) to create trajectories that are effective, optimal, efficient, safe, fast and most suitable for the purpose (e.g. the a priori information may use an expected anatomical geometry to generate a trajectory that minimized unnecessary or redundant vantage points). The Trajectory Planning Module 1602 may further consider other constraints or inputs, such as inputs to increase safety for the patient and/or operator by avoiding certain end effector poses; incorporating data from a force feedback and or range-finding sensor and adjusting trajectories using the data etc.). In one implementation, there may be a Trajectory Planning module for generating a commanded trajectory for a robotic system to generate a 3D surface scan of an anatomy using the following computer implemented method 1650 illustrated in FIG. 16B:

Receiving a pose of a robotic end-effector having a 3D scanning camera and structured light projector coupled thereto (1652);
Receiving 3D scan data from the 3D scanning camera based on reflected structured light (1654);
Estimating a relative pose of the end effector and the anatomy, based on either i) an initial pose estimate, or ii) the 3D scan data (1656);
Accessing registration data criteria (1658);
Generating metrics corresponding to the registration data criteria based at least in part on the 3D scan data (1660);
Where the metrics do not meet the registration data criteria, determining an updated trajectory to improve the metrics by moving the 3D scanning camera via the end-effector to a new pose, based on at least the estimated relative pose and the 3D scan data (1662); and
Providing the updated commanded trajectory as an input to the robot control system (1664).

Application to robotic surgery has been presented with a 3D scanning system, in which the structured light projector is fixed relative to a camera. This arrangement is meant to be exemplary. Other scanning modalities are also contemplated.

Figure 16A:
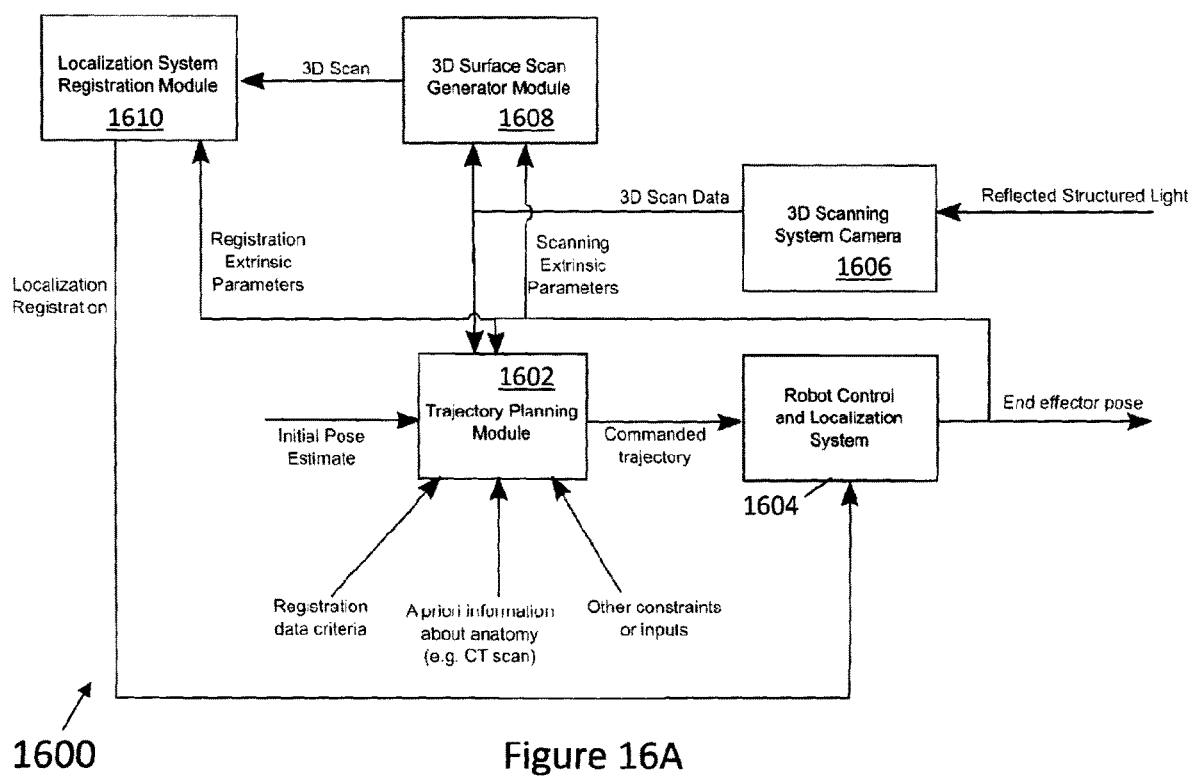
FIG. 16A illustrates a block diagram of a computer system having a Trajectory Planner for a robot.
Figure 16B:
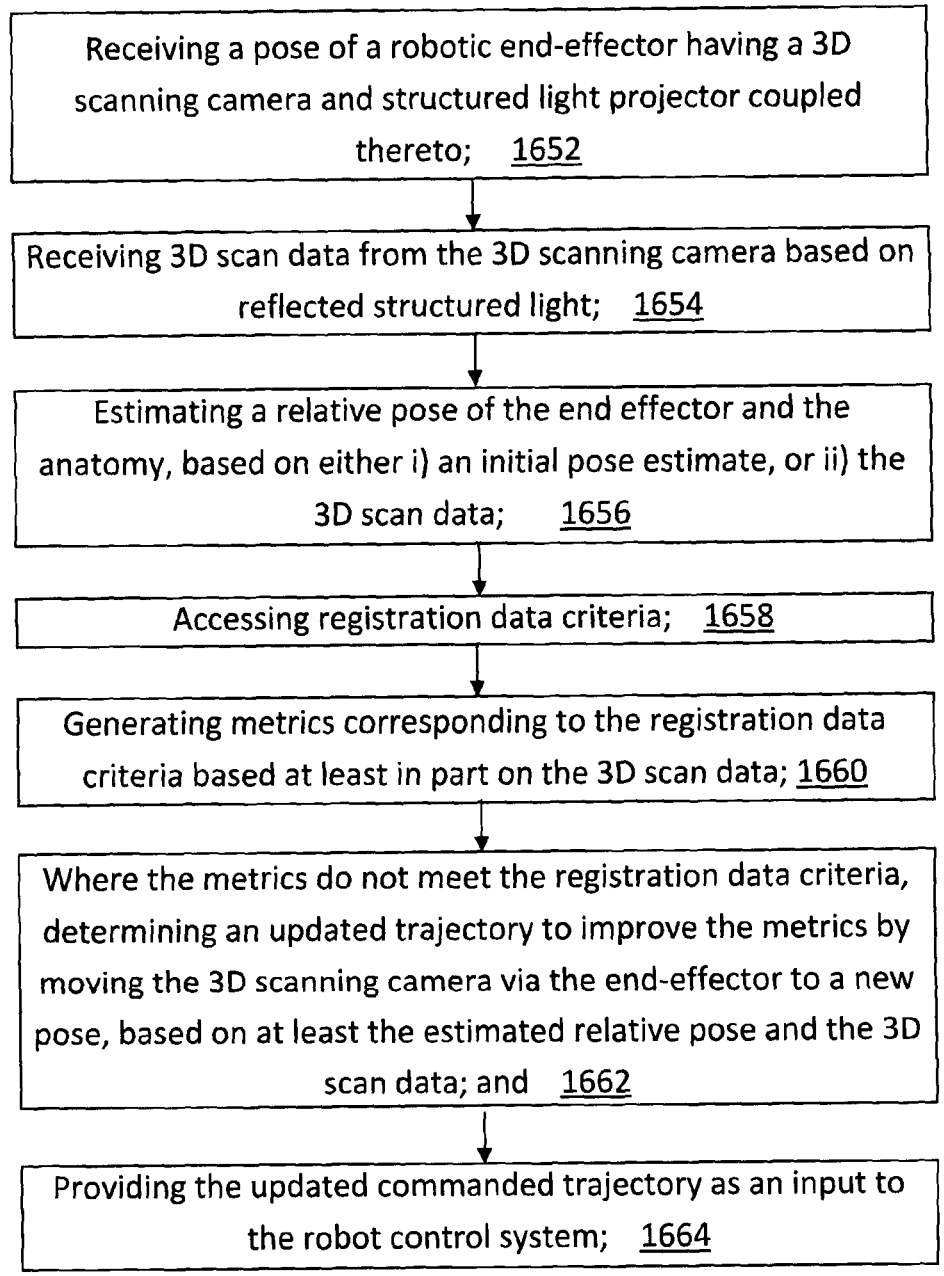
FIG. 16B shows a flowchart of a computer implemented method.

With further reference to FIG. 16A, Trajectory Planning Module 1602 aids in generating a 3D scan that is used, in combination with registration extrinsic parameters (based on end-effector pose), by a Localization System Registration Module 1610 (similar to that described above) to generate an accurate registration between the 3D scan and the localization system. After receiving the localization registration, the Robotic Control and Localization system 1604 may operate in a localization mode, in which commanded trajectories are no longer based on the Trajectory Planning Module 1602, but instead, based on another module used to effect a desired pose of the robotic tool (such as a high speed burr) with respect to the patient's anatomy.

Figure 17:
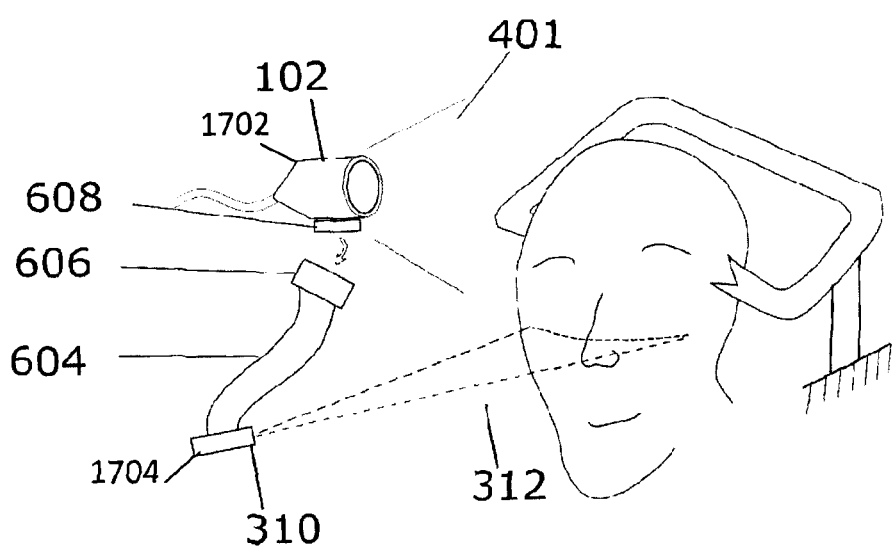
FIG. 17 depicts a 3D scanning system with an inertial sensor.

Inertial sensors (e.g. accelerometers, gyroscopes) and possibly other sensors (such as magnetometers) can be incorporated into the 3D scanning system. The 3D scanning system comprises a camera and a structured light projector to generate 3D scan data. As illustrated in FIG. 17, inertial sensors (e.g. 1702, 1704) can be integrated either into the camera or the structured light projector and inertial sensor data can be provided to a computing unit. The inertial sensor data is used by the computing unit to calculate the scanning extrinsic parameters.

One limitation of inertial sensing is that position and orientation measurement based solely on inertial sensing data is subject to drift because some inertial signals that include noise are integrated to estimate position and/or orientation. The scanning extrinsic parameters are generated by the computing unit based on the inertial sensor data as well as additional optical data provided by the camera (e.g. the 3D scan data). The additional optical data is used to alleviate or partially alleviate the susceptibility of the scanning extrinsic parameters to drift. This may be implemented computationally as follows: the 3D scan data comprises a multitude of points in 3D space; a feature of the anatomy (e.g. in the form of a point, a collection of points, etc.) is identified in two sequential images—a first image and a second image; scanning extrinsic parameter data is received corresponding to the two sequential images; a relative pose based on the scanning extrinsic parameters is computed between the two sequential images; the relative pose is applied to the feature of the anatomy in the first image, and then compared to the second image (i.e. a spatial difference is computed); the spatial difference is used to compute a pose correction factor, the pose correction factor is applied to the scanning extrinsic parameters to compensate for error due to drift. Additionally, a priori information about the anatomy (e.g. via a medical image) may be used by the computing unit to compensate for inertial sensor drift, thus enabling a 3D surface scan and image registration based on scanning extrinsic parameters generated using inertial sensors. For example, this may be done as follows: a 3D surface scan using scanning extrinsic parameters that utilize inertial sensors may be generated. Each of the 3D points that are a part of the 3D surface scan may have associated temporal data (e.g. a time stamp). Due to drift from the inertial sensors in the calculation of position and orientation, the 3D surface scan may be warped (i.e. not representing a true 3D surface profile). An additional computation module may receive as inputs: the warped 3D scan, the temporal data associated with each point in the scan, and a 3D model (e.g. from a medical image) with an accurate representation of the 3D surface profile. The module performs an optimization routine that estimates the drift based on the temporal data and uses the inputs to generate an unwrapped 3D surface scan with an adjusted the location of points in the 3D surface scan to minimize euclidean distance between points of the 3D surface scan and the 3D model.

The 3D scanning system may be further configured to identify a type of material in the surface profile that is being scanned. The 3D surface scan of the anatomy would then include not only the spatial surface profile, but also data at each location of the scanned surface indicating the type of tissue or material at that location. For example, in reference to FIG. 18, a knee incision 1802 exposed for knee surgery is illustrated. Materials shown include: bone (tibia 1804, femur 1806, osteophytes 1808), cartilage 1810 (on the tibial plateau and femoral epicondyles), subcutaneous fat 1812, muscle 1814, and metal 1816 (of the retractors). While 3D scanning the exposed knee, the system may be configured to generate and provide data about the type of tissue/material at each location in the scan. This may be useful to filter out disturbances (e.g. the goal is to generate a surface profile of the articular surface, locations within the 3D scan not identified as cartilage may be excluded from further computations). An exposed knee is provided as an example, but this may be done for any location on the body/any tissue (e.g. identifying hair in a cranial 3D scan, identifying tumors in tumor resection surgery, etc.).

Various technologies may be applied to ascertain the material/tissue being 3D scanned such as, spectroscopic technologies and techniques. It is important to establish a correspondence between the 3D scan data, and signals representing the material properties (i.e. the material properties being indicative of the type of material). For example, a sensor that senses the material properties may be co-registered to the scanning system while sensing the material properties of the surface being 3D scanned. The sensor that senses material properties may be rigidly attached to the 3D scanning apparatus (e.g. the camera and structured light projector), and the sensor may be pointing in the same direction as the projected structured light and the camera.

Figure 18:
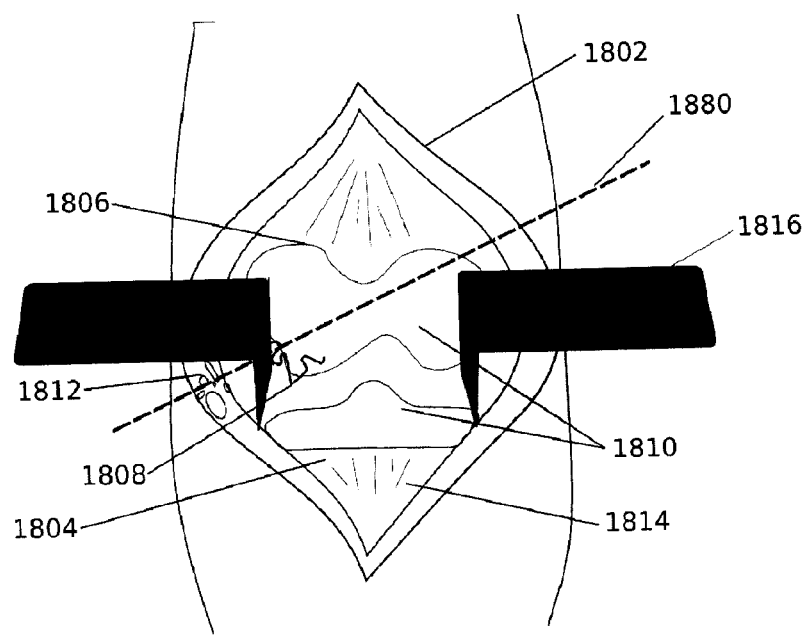
FIG. 18 depicts a patient's knee exposed with a retractor.

Structured light from the structured light projector of the 3D scanning system (e.g. as seen in FIG. 11A) may interact with different materials differently (e.g. intensity of reflections) and the camera may detect the differences in the interaction. The structured light may contain various frequencies or spectra of light that interact with various materials differently. The camera may be a multi-spectral camera (i.e. the camera being able to independently measure optical signals in certain spectral bands, channels and/or wavelengths). A colour camera may be used, in which the colour of the material/tissue provides information to determine the type of material. Dyes or other markings may be used to aid in preparing the scanning surface to respond to structured light in a way that can then be detected. The computing unit, connected to the camera, may determine the characteristics/properties/type of material or tissue based on the 3D scan data (which may be multi-spectral), and based on a priori data correlating the type of material/tissue with the corresponding expected reflected light. In FIG. 18, a projection of structured light 1880 projected onto various materials/tissues, including: metal (retractors); bone (osteophytes); cartilage (epicondyles); and fat.

The computing unit may generate a 3D surface scan that includes information about the type of material/tissue at each location along the surface of the scan, and provide the 3D surface scan for further processing, or for display to a user. When displayed to a user, the 3D surface scan may omit certain types of materials/tissues from display (automatically or as selected by a user). The 3D scan may further be displayed to visually distinguish the types of tissue/material in a graphical representation (e.g. by using different patterns and/or colours).

The 3D surface scan that includes spectroscopic information may be further processed by the computing unit. For example, an articular surface of a joint may be identified and processed to determine the native kinematics of the joint. The native kinematics may be determined by the computing unit with respect to the localization system. The computing unit may recommend a surgical plan and/or surgical targets based on the native kinematics.

It is apparent that numerous systems, devices and methods aspects are provided herein. Unless otherwise stated portions of various systems may be implemented on shared hardware or using shared peripherals such as cameras, trackers, etc. In some instances peripherals may be coupled to one computing system at one time (e.g. to perform a 3D scan) and then to another (e.g. to perform tracking and navigation, etc.) at another time. Variations will be apparent to a person of ordinary skill in the art.

What is claimed is:

1. A computer-implemented method, comprising steps of:
   receiving a pose of a robotic end-effector having a 3D scanning camera and structured light projector coupled thereto;
   receiving 3D scan data of patient anatomy from the 3D scanning camera based on reflected structured light generated by the structured light projector;
   estimating a relative pose of the end effector and the anatomy, based on either i) an initial pose estimate, or ii) the 3D scan data;
   accessing registration data criteria;
   generating metrics corresponding to the registration data criteria based at least in part on the 3D scan data;
   when the metrics do not meet the registration data criteria:
   determining an updated trajectory to improve the metrics by moving the 3D scanning camera via the end-effector to a new pose, based on at least the estimated relative pose and the 3D scan data; and
   providing the updated commanded trajectory as an input to a robot control system to move the end effector.

2. The method of claim 1 further comprising, when the metrics meet the registration data criteria, completing a registration of the 3D surface scan to the robotic control system.

3. The method of claim 2 comprising further completing a registration of the 3D surface scan to a medical image and/or anatomical model for the patient anatomy.

4. The method of claim 1 further comprising repeating the steps of the method until the metrics meet the registration data criteria.

5. The method of claim 1, wherein registration data criteria includes any one or more of: a correlation of aggregated 3D scan data with an expected surface profile obtained from a medical image; a spatial and/or angular coverage obtained in the 3D scan data with respect to the anatomy; a density of 3D scan data with respect to the anatomy.

6. The method of claim 1 comprising receiving a priori information about the patient anatomy to create optimized trajectories, minimizing unnecessary or redundant vantage points of the patient anatomy.

7. The method of claim 1 comprising one or both of:
   receiving other constraints or inputs, to increase safety by avoiding certain end effector poses; and
   receiving data from a force feedback and or range-finding sensor and adjusting the updated trajectory in response.

8. A computing system comprising a processor and a non-transient storage medium storing instructions which, when executed by the processor, cause the computing system to:
   receive a pose of a robotic end-effector having a 3D scanning camera and structured light projector coupled thereto;
   receive 3D scan data of patient anatomy from the 3D scanning camera based on reflected structured light generated by the structured light projector;
   estimate a relative pose of the end effector and the anatomy, based on either i) an initial pose estimate, or ii) the 3D scan data;
   access registration data criteria;
   generate metrics corresponding to the registration data criteria based at least in part on the 3D scan data;
   when the metrics do not meet the registration data criteria:
   determine an updated trajectory to improve the metrics by moving the 3D scanning camera via the end-effector to a new pose, based on at least the estimated relative pose and the 3D scan data; and
   provide the updated commanded trajectory as an input to a robot control system to move the end effector.

9. The computing system of claim 8, wherein the instructions further cause the computer to, when the metrics meet the registration data criteria, complete a registration of the 3D surface scan to the robotic control system.

10. The computing system of claim 9, wherein the instructions further cause the computer to further complete a registration of the 3D surface scan to a medical image and/or anatomical model for the patient anatomy.

11. The computing system of claim 8, wherein registration data criteria includes any one or more of: a correlation of aggregated 3D scan data with an expected surface profile obtained from a medical image; a spatial and/or angular coverage obtained in the 3D scan data with respect to the anatomy; a density of 3D scan data with respect to the anatomy.

12. The computing system of claim 8, wherein the instructions further cause the computer to receive a priori information about the patient anatomy to create optimized trajectories, minimizing unnecessary or redundant vantage points of the patient anatomy.

13. The computing system of claim 8, wherein the instructions further cause the computer to, one or both of:

receive other constraints or inputs, to increase safety by avoiding certain end effector poses; and receive data from a force feedback and or range-finding sensor and adjusting the updated trajectory in response.

14. A computer program product comprising a non-transient storage medium storing instructions that, when executed by a processor of a computing system, cause the computing system to:

receive a pose of a robotic end-effector having a 3D scanning camera and structured light projector coupled thereto;

receive 3D scan data of patient anatomy from the 3D scanning camera based on reflected structured light generated by the structured light projector;

estimate a relative pose of the end effector and the anatomy, based on either i) an initial pose estimate, or ii) the 3D scan data;

access registration data criteria;

generate metrics corresponding to the registration data criteria based at least in part on the 3D scan data;

when the metrics do not meet the registration data criteria:
determine an updated trajectory to improve the metrics by moving the 3D scanning camera via the end-effector to a new pose, based on at least the estimated relative pose and the 3D scan data; and provide the updated commanded trajectory as an input to a robot control system to move the end effector.

15. The computer program product of claim 14, wherein the instructions further cause the computer to, when the metrics meet the registration data criteria, complete a registration of the 3D surface scan to the robotic control system.

16. The computer program product of claim 15, wherein the instructions further cause the computer to further complete a registration of the 3D surface scan to a medical image and/or anatomical model for the patient anatomy.

17. The computer program product of claim 14, wherein registration data criteria includes any one or more of: a correlation of aggregated 3D scan data with an expected surface profile obtained from a medical image; a spatial and/or angular coverage obtained in the 3D scan data with respect to the anatomy; a density of 3D scan data with respect to the anatomy.

18. The computer program product of claim 14, wherein the instructions further cause the computer to receive a priori information about the patient anatomy to create optimized trajectories, minimizing unnecessary or redundant vantage points of the patient anatomy.

19. The computer program product of claim 14, wherein the instructions further cause the computer to, one or both of:

receive other constraints or inputs, to increase safety by avoiding certain end effector poses; and receive data from a force feedback and or range-finding sensor and adjusting the updated trajectory in response.

* * * * *